United States Patent
McCullough

(10) Patent No.: US 9,932,423 B2
(45) Date of Patent: Apr. 3, 2018

(54) HYDROGENATION OF ANNULATED CYCLOPENTADIENYL METAL COMPLEXES AND METALLOCENE CATALYSTS COMPRISING SUCH

(71) Applicant: ExxonMobil Chemical Patents Inc., Baytown, TX (US)

(72) Inventor: Laughlin G. McCullough, League City, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/238,448

(22) Filed: Aug. 16, 2016

(65) Prior Publication Data

US 2017/0088643 A1 Mar. 30, 2017

Related U.S. Application Data

(60) Provisional application No. 62/222,926, filed on Sep. 24, 2015.

(51) Int. Cl.
*C07F 17/00* (2006.01)
*C08F 4/6592* (2006.01)
*C08F 110/02* (2006.01)

(52) U.S. Cl.
CPC ........... *C08F 110/02* (2013.01); *C07F 17/00* (2013.01); *C08F 4/6592* (2013.01); *C08F 4/65927* (2013.01)

(58) Field of Classification Search
CPC ..... C07F 17/00; C08F 4/6592; C08F 4/65927
See application file for complete search history.

(56) References Cited

U.S. PATENT DOCUMENTS

| | | |
|---|---|---|
| 5,670,680 A | 9/1997 | Newman et al. |
| 5,760,680 A | 6/1998 | Hwang |
| 5,883,275 A | 3/1999 | Bingel et al. |
| 6,153,549 A | 11/2000 | Hubscher et al. |
| 6,541,584 B1 | 4/2003 | Resconi |

FOREIGN PATENT DOCUMENTS

| | | |
|---|---|---|
| EP | 530 908 | 3/1993 |
| EP | 780 395 | 6/1997 |
| EP | 839 823 | 5/1998 |
| WO | WO 2010/077163 | 7/2010 |

OTHER PUBLICATIONS

Bandy, J.A. et al., "Polymerisation of Ethylene and Propene using New Chiral Zirconium Derivatives. Crystal Structure of $[ZrL^1Cl_2]$-$[H_2L^1=(4S,5S)$-trans-4,5-bis(1H-inden-1-ylmethyl)-2,2-dimethyl-1,3-dioxolane]," J. Chem. Soc. Dalton Trans., 1991, pp. 2207-2216.
Erker, G. et al., "Hydroboration of Bis(alkenylcyclopentadienyl)zirconium Dichlorides," Chem. Ber., 1991, vol. 124, pp. 1301-1310.
Erker, G. et al., "Cp-Substituent Additivity Effects Controlling the Stereochemistry of the Propene Polymerization Reaction at Conformationally Unrestricted $(Cp-CHR^1R^2)_2ZrCl2/$Methylalumoxane Catalysts," J. Am. Chem. Soc., 1991, vol. 113(20), pp. 7594-7602.
Erker, G. et al., "Synthesis of ansa-Metallocenes by Intramolecular Photochemical [2+2] Cycloaddition of Bis(alkenylcyclopentadienyl)zirconium Complexes," Organometallics, 1993, vol. 12(6), pp. 2140-2151.
Hollis, T.K. et al., "Preparation and Properties of (S,S)-[Ti((R,R)-cyclacene)$Cl_2$], a Chiral Strapped Bent Metallocene," Organometallics, 1992, vol. 11(8), pp. 2812-2816.
Larsonneur, A.M. et al., "Synthesis, Characterization, and Chemical Reactivity of Zirconium Dihydride $[(C_5H_4R)_2Zr(u-H)H]_2$ $(R=SiMe_3,CMe_3)$. H/D Exchange Reactions of Anionic Species $[(C_5H_4R)_2ZrH_2]^-$. X-ray Crystal Structure of $[(C_5H_4SiMe_3)_2Zr(u-H)H]_2$," Organometallics, 1993, vol. 12(8), pp. 3216-3224.
Ogasawara, M. et al., "Metathesis Route to Bridged Metallocenes," Jrnl. Amer. Chem Soc., 2002, vol. 124(31), pp. 9068-9069.
Rheingold, A.L. et al., "Preparation and Properties of Chiral Titanocene and Zirconocene Dichloride Complexes of a Chiral Ligand," Organometallics, 1992, vol. 11(5), pp. 1869-1876.
Schafer, A. et al., "ansa-Metallocene Derivatives," Jrnl. of Organometallic Chemistry, 1987, vol. 328, pp. 87-99.
Sornay, C. et al., "Stereoselective Access to the Three Diisodicyclopentadlenyltitanium Dichlorides," Organometallics, 1991, vol. 10(6), pp. 2082-2083.
Wild, F.R.W.P. et al., "ansa-Metallocene Derivatives," Jrnl. of Organometallic Chemistry, 1982, vol. 232, pp. 233-247.

*Primary Examiner* — Caixia Lu

(57) ABSTRACT

Disclosed are methods for making partially hydrogenated annulated cyclopentadienyl complexes which can provide efficient synthesis of metallocene catalysts desired for olefin polymerization.

25 Claims, No Drawings

HYDROGENATION OF ANNULATED CYCLOPENTADIENYL METAL COMPLEXES AND METALLOCENE CATALYSTS COMPRISING SUCH

CROSS REFERENCE TO RELATED APPLICATIONS

This invention claims priority to and the benefit of U.S. Ser. No. 62/222,926, filed Sep. 24, 2015.

FIELD OF THE INVENTION

This invention relates to methods for preparing partially hydrogenated annulated cylopentadienyl metal complexes, metallocene catalysts comprising such, and catalyst systems made thereby.

BACKGROUND OF THE INVENTION

Olefin polymerization catalysts are of great use in industry. Hence, there is a growing interest in exploring new catalyst systems and efficient methods for manufacturing such catalysts. Catalysts for olefin polymerization are often based on metallocenes as catalyst precursors, which are typically activated either with the help of an alumoxane, or with an activator containing a non-coordinating anion.

A metallocene catalyst component often appears in two stereo-isomeric forms: a racemic form and a meso form. A stereospecific catalyst is generally used to prepare stereoregular polyolefins. The racemic form induces a reproducible orientation of incoming monomers when the catalyst component is used in an olefin polymerization reaction. This is desirable for producing an isotactic polyolefin. Efforts have been made either to avoid the production of the meso isomer or to separate the desirable racemic isomer from the meso isomer, but the separation step is costly and it has been observed that after purification the meso isomer is reintroduced in the system under the effect of light or heat. Hydrogenation of the catalyst component avoids the formation of the meso isomer and/or its "re-formation" under the effect of light or heat. As such, a hydrogenated metallocene catalyst component is favorable in olefin polymerization.

Synthesis of hydrogenated or partially hydrogenated metallocenes generally starts from the corresponding metallocenes having aromatic ligands. The metallocene is dissolved or suspended in dichloromethane and hydrogenated in the presence of platinum black or platinum dioxide under a high pressure of hydrogen. An alternative to the above synthesis can be hydrogenation of metal complexes, followed by reaction with cyclopentadiene. Examples include metallocenes possessing 4,5,6,7-tetrahydroindenyl groups that are widely used in preparation of stereoregular polyolefins, for example, cyclopentadienyl tetrahydroindenyl metal complexes obtained by hydrogenation of corresponding cyclopentadienyl indenyl metal complexes.

WO 2010/077163 relates to the synthesis of substituted tetrahydroindenyls and the use of the synthesized complexes in the homo- and co-polymerization of ethylene and α-olefins.

U.S. Pat. No. 6,541,584 provides a class of bridged bis(tetrahydroindenyl)metallocenes of Formula (I), wherein M is Zr or Hf; X are monoanionic sigma ligands; $(ZR^1_i)_j$ is a divalent group bridging the two tetrahydroindenyl residues; $R^2$ and $R^3$ are halogen, alkyl, cycloalkyl, aryl, alkylaryl, or arylalkyl radicals; p is 0-3; i is 1 or 2; j is 1-4; m is 1-2; and n is 0-8. Furthermore, catalyst systems for olefin polymerization containing them are described.

U.S. Pat. No. 5,883,275 discloses a process for the hydrogenation of metallocenes, which comprises treating at least one metallocene containing at least one double bond and/or at least one aromatic substituent in at least one nonhalogenated solvent with hydrogen in the presence of at least one hydrogenation catalyst.

In view of the above, it will be understood that there is a further need in the art for improved routes to prepare a hydrogenated metallocene catalyst for olefin polymerization, which catalyst can facilitate polymerization of olefins to high isotacticity.

The inventor has found that, starting from annulated cyclopentadienyl metal complexes of the type $(J)_p CpMX_nL_m$ (Cp=cyclopentadienyl), as defined below, corresponding hydrogenated metal complexes $(JH)_p CpMX_nL_m$, as defined below, can be conveniently formed by hydrogenation, which can be subsequently converted to metallocene catalysts of the type $Cp((JH)_pCp)MX_2$, as defined below, for use in catalysis of olefin polymerization. In contrast with the commonly used synthesis of tetrahydroindenyl metal complexes starting with tetrahydroindenide compounds, which is very time-consuming (a six-step process) and low in yield, for example, the present invention can provide an easy and high-yield alternative for preparing tetrahydroindenyl metal compounds, which can be useful in efficient catalysts for olefin polymerization.

Examples of transformations of the coordinated cyclopentadienyl ligands of Group 4 metal complexes resulting in no modification of the nearest coordination polyhedron have been described, e.g., H/D exchange in $\eta^5$-cyclopentadienyls (Larsonneur, A.-M.; Choukroun, R.; Jaud, J. Organometallics 1993, 12, 3216); Pd/C or $PtO_2$ catalyzed hydrogenation of $\eta^5$-indenyls giving $\eta^5$-tetrahydroindenyls (Wild, F. R. W. P.; Zsolnai, L.; Huttner, G.; Brintzinger, H. H. J. Organomet. Chem. 1982, 232, 233. Schafer, A.; Karl, E.; Zsolani, L.; Huttner, G.; Brintzinger, H. H. J. Organomet. Chem. 1987, 328, 87. Bandy, J. A.; Green, M. L. H.; Gardiner, I. M.; Prout, K. J. Chem. Soc., Dalton Trans. 1991, 2207. Rheingold, A. L.; Robinson, N. P.; Whelan, J.; Bosnich, B. Organometallics 1992, 11, 1869. Hollis, T. K.; Rheingold, A. L.; Robinson, N. P.; Whelan, J.; Bosnich, B. Organometallics, 1992, 11, 2812); hydroboration of allyl- and vinyl-$\eta^5$-cyclopentadienyl complexes (Erker, G.; Nolfe, R.; Aul, R.; Wilker, S.; Kruger, C.; Noe, R. J. Am. Chem. Soc. 1991, 113, 7594. Erker, G.; Aul, R. Chem. Ber. 1991, 124, 1301); intramolecular photochemical [2+2] cycloaddition of vinyl-$\eta^5$-cyclopentadienyl complexes (Erker, G.; Wilker, S.; Kruger, C.; Nolte, M. Organometallics 1993, 12, 2140); Ru-catalyzed metathesis of bis(allyl-$\eta^5$-cyclopentadienyl) zirconium and -hafnium dichlorides (Ogasawara, M.; Nagano, T.; Hayashi, T. J. Am. Chem. Soc., 2002, 124, 9068).

SUMMARY OF THE INVENTION

The inventor has found that, starting from annulated cyclopentadienyl metal complexes of the type $(J)_p CpMX_nL_m$, (such as indene) corresponding hydrogenated metal complexes $(J*H)_p CpMX_nL_m$, can be conveniently formed by hydrogenation, which can be subsequently converted to metallocene catalysts of the type $Cp((J*H)_pCp) MX_2$, where: Cp is cyclopentadienyl;

J is C—R, CH, HC—R, $CR_2$ or $CH_2$, such that $(J)p$ is $C_3$ to $C_{30}$ substituted or unsubstituted hydrocarbyl group having a chain of 3, 4, 5, or 6 carbons bound to two adjacent carbon atoms on the Cp to form a substituted or unsubstituted aromatic or pseudo aromatic 5, 6, 7, or 8 membered ring, which may be substituted or unsubstituted;

J* is C, C—R, CH, such that (J*H)$_p$ is a C$_3$ to C$_{30}$ substituted or unsubstituted hydrocarbyl group having a chain of 3, 4, 5, or 6 carbons bound to two adjacent carbon atoms on the Cp to form a substituted or unsubstituted saturated 5, 6, 7, or 8 membered ring;

p is 3, 4, 5, or 6;

n is 1, 2, 3, 4, or 5;

m is 1, 2, 3, or 4;

M is a transition metal belonging to group 3, 4, 5, 6 or to the lanthanide or actinide groups of the Periodic Table of the Elements;

the X groups, the same or different from each other, are monoanionic ligands selected from the group consisting of hydrogen, halogen, —R, —OR, —OSO$_2$CF$_3$, —OCOR, —SR, —NR$_2$, and —PR$_2$ groups;

the R substituents, the same or different from each other, are linear or branched, saturated or unsaturated, C$_1$-C$_{20}$ alkyl, C$_3$-C$_{20}$ cycloalkyl, C$_6$-C$_{20}$ aryl, C$_7$-C$_{20}$ alkylaryl, or C$_7$-C$_{20}$ arylalkyl radicals, optionally containing one or more atoms belonging to groups 13-17 of the Periodic Table of the Elements, and two R substituents may form a 5-7 membered ring; and and the L groups, the same or different from each other, are neutral donor ligands.

A process for preparing polyethylene comprising contacting ethylene with the catalyst system described herein and obtaining polyethylene is also provided.

DETAILED DESCRIPTION OF THE INVENTION

Various specific embodiments, versions of the present invention will now be described, including preferred embodiments and definitions that are adopted herein. While the following detailed description gives specific preferred embodiments, those skilled in the art will appreciate that these embodiments are exemplary only, and that the present invention can be practiced in other ways. Any reference to the "invention" may refer to one or more, but not necessarily all, of the present inventions defined by the claims. The use of headings is for purposes of convenience only and does not limit the scope of the present invention.

For the purposes of this invention and the claims thereto, the new numbering scheme for the Periodic Table Groups is used as described in Chemical and Engineering News, 63(5), p. 27 (1985). Therefore, a "Group 4 metal" is an element from Group 4 of the Periodic Table, e.g., Hf, Ti, or Zr.

An "olefin," alternatively referred to as an "alkene," is a linear, branched, or cyclic compound of carbon and hydrogen having at least one double bond. For purposes of this specification and the claims appended thereto, when a polymer or copolymer is referred to as comprising an olefin, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. A "terpolymer" is a polymer having three mer units that are different from each other. "Different" as used to refer to mer units indicates that the mer units differ from each other by at least one atom or are different isomerically. Accordingly, the definition of copolymer, as used herein, includes terpolymers and the like. An "ethylene polymer" or "ethylene copolymer" is a polymer or copolymer comprising at least 50 mol % ethylene derived units, a "propylene polymer" or "propylene copolymer" is a polymer or copolymer comprising at least 50 mol % propylene derived units, and so on.

For the purposes of this invention, ethylene shall be considered an α-olefin.

For purposes of this invention and claims thereto, unless otherwise specified, the term "substituted" means that a hydrogen group has been replaced with a heteroatom, or a heteroatam-containing group. For example, a "substituted hydrocarbyl" is a radical made of carbon and hydrogen where at least one hydrogen is replaced by a heteroatom or heteroatam-containing group.

As used herein, Mn is number average molecular weight, Mw is weight average molecular weight, and Mz is z average molecular weight, wt % is weight percent, and mol % is mole percent. Molecular weight distribution (MWD), also referred to as polydispersity (PDI), is defined to be Mw divided by Mn, measured using a gel permeation chromatograph ("GPC") equipped with a differential refractive index ("DRI") detector. Unless otherwise noted, all molecular weight units (e.g., Mw, Mn, Mz) are g/mol.

The following abbreviations may be used herein: Me is methyl, Et is ethyl, Pr is propyl, cPR is cyclopropyl, nPr is n-propyl, iPr is isopropyl, Bu is butyl, nBu is normal butyl, iBu is isobutyl, sBu is sec-butyl, tBu is tert-butyl, Oct is octyl, Ph is phenyl, Bn is benzyl, MAO is methylalumoxane, Ind is indenyl, Cp is cyclopentadienyl, Flu is fluorenyl, OTf is triflate, RT is room temperature (23° C., unless otherwise indicated).

As used herein, a "catalyst system" is a combination of at least one catalyst compound, at least one activator, an optional co-activator, and an optional support material. For the purposes of this invention and the claims thereto, when catalyst systems are described as comprising neutral stable forms of the components, it is well understood by one of ordinary skill in the art, that the ionic form of the component is the form that reacts with the monomers to produce polymers.

As used herein, the metallocene catalyst may be described as a catalyst precursor, a pre-catalyst compound, metallocene catalyst compound, or a transition metal compound, and these terms are used interchangeably. A polymerization catalyst system is a catalyst system that can polymerize monomers to polymer. An "anionic ligand" is a negatively charged ligand which donates one or more pairs of electrons to a metal ion. A "neutral donor ligand" is a neutrally charged ligand which donates one or more pairs of electrons to a metal ion.

A metallocene catalyst is defined herein as an organometallic compound with at least one π-bound cyclopentadienyl moiety (or substituted cyclopentadienyl moiety) and more frequently two π-bound cyclopentadienyl moieties or substituted cyclopentadienyl moieties.

For purposes of this invention and claims thereto in relation to metallocene catalyst compounds and J or J*, the term "substituted" means that a hydrogen group has been replaced with a hydrocarbyl group, a heteroatom, or a heteroatam-containing group. For example, methyl cyclopentadiene (Cp) is a Cp group substituted with a methyl group.

The terms "hydrocarbyl radical," "hydrocarbyl" and "hydrocarbyl group" are used interchangeably throughout this document. Likewise, the terms "group," "radical," and "substituent" are also used interchangeably in this document. For purposes of this disclosure, "hydrocarbyl radical" is defined to be a radical, which contains hydrogen atoms and up to 100 carbon atoms and which may be linear, branched, or cyclic, and when cyclic, aromatic or non-aromatic. A "substituted hydrocarbyl" is a radical made of carbon and hydrogen where at least one hydrogen is replaced by a heteroatom or heteroatam-containing group.

The term "aromatic" is defined to mean a planar cyclic hydrocarbyl group having conjugated double bonds, such as benzene, cyclopentadiene, napthylene, anthracene, indene, and fluorene.

The term "pseudoaromatic" refers to substituents that have similar properties and structures (nearly planar) to aromatic groups, but are not by definition aromatic, such as cyclooctene, cyclohexadiene, and cyclooctatriene.

The term "aryl" or "aryl group" means a six-carbon aromatic ring and the substituted variants thereof, including but not limited to, phenyl, 2-methyl-phenyl, xylyl, and 4-bromo-xylyl. Likewise, heteroaryl means an aryl group where a ring carbon atom (or two or three ring carbon atoms) has been replaced with a heteroatom, preferably N, O, or S.

The term "continuous" means a system that operates without interruption or cessation. For example, a continuous process to produce a polymer would be one where the reactants are continually introduced into one or more reactors and polymer product is continually withdrawn.

Methods for Preparing Partially Hydrogenated Annulated Cyclopentadienyl Complexes The present invention relates to a method for preparing partially hydrogenated annulated cyclopentadienyl complexes, comprising contacting: (a) a complex of Formula (I):

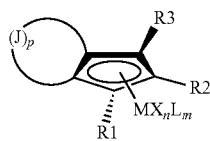

wherein:
J is C—R, CH, HC—R, $CR_2$ or $CH_2$, such that $(J)p$ is $C_3$ to $C_{30}$ substituted or unsubstituted hydrocarbyl group having a chain of 3, 4, 5, or 6 carbons bound to the Cp to form an aromatic or pseudoaromatic 5, 6, 7 or 8 membered ring, which may be substituted or unsubstituted (preferably $(J)p$ is —$(C_3H_4)$—, —$(C_4H_4)$—, —$(C_5H_6)$—, —$(C_6H_6)$—);
p is 3, 4, 5, or 6, preferably 3;
n is 1, 2, 3, 4, or 5;
m is 1, 2, 3, or 4;
M is a transition metal belonging to group 3, 4, 5, 6 or to the lanthanide or actinide groups of the Periodic Table of the Elements, preferably a group 4 metal, preferably Hf, Zr, or Ti;
the X groups, the same or different from each other, are monoanionic ligands selected from the group consisting of hydrogen, halogen, —R, —OR, —$OSO_2CF_3$, —OCOR, —SR, —$NR_2$, and —$PR_2$ groups, preferably X is a C1 to C20 alkyl or halogen, such as chlorine, bromine, iodine, fluorine, methyl, ethyl, propyl, butyl, pentyl, hexyl, heptyl, octyl, nonyl, decyl, undecyl, dodecyl, or an isomer thereof;
the R substituents, the same or different from each other, are linear or branched, saturated or unsaturated, $C_1$-$C_{20}$ alkyl, $C_3$-$C_{20}$ cycloalkyl, $C_6$-$C_{20}$ aryl, $C_7$-$C_{20}$ alkylaryl, or $C_7$-$C_{20}$ arylalkyl radicals, optionally containing one or more atoms belonging to Groups 13-17 of the Periodic Table of the Elements, and two R substituents may form a 5-7 membered ring, preferably R is methyl, ethyl, propyl, butyl, pentyl, hexyl, heptyl, octyl, nonyl, decyl, undecyl, dodecyl, or an isomer thereof;
the L groups, the same or different from each other, are neutral donor ligands; and $R^1$, $R^2$ and $R^3$ are each independently a hydrogen atom or a substituted or unsubstituted $C_1$ to $C_{20}$ hydrocarbyl group, and, optionally, $R^1$ and $R^2$ or $R^2$ and $R^3$ can be joined to form a cyclic structure, preferably methyl, ethyl, propyl, butyl, pentyl, hexyl, heptyl, octyl, nonyl, decyl, undecyl, dodecyl or an isomer thereof; with (b) hydrogen and a hydrogenation catalyst to obtain a complex of Formula (II):

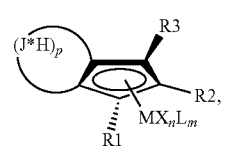

wherein:
M, X, L, n, m, p, R, $R^1$, $R^2$, and $R^3$, are as defined for Formula (I) and J* is C, C—R, CH, such that $(J*H)_p$ is a $C_3$ to $C_{30}$ substituted or unsubstituted hydrocarbyl group having a chain of 3, 4, 5, or 6 carbons bound to the Cp to form a substituted or unsubstituted saturated 5, 6, 7, or 8 membered ring, (preferably $(J*)p$ is —$(C_3H_6)$—, —$(C_4H_8)$—, —$(C_5H_{10})$—, or —$(C_6H_{12})$—).

In another embodiment, the present invention relates to a method for preparing a tetrahydroindenyl, comprising the steps of: (a) contacting a complex of Formula (III):

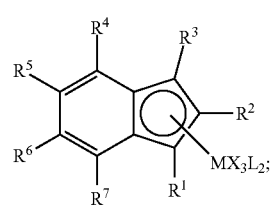

(b) with hydrogen and a hydrogenation catalyst to prepare a complex of Formula (IV):

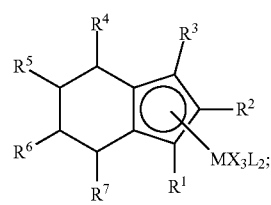

where M is a transition metal belonging to group 3, 4, 5, 6, or to the lanthanide or actinide groups of the Periodic Table of the Elements (preferably Hf, Zr, or Ti);
the X groups, the same or different from each other, are monoanionic sigma ligands selected from the group consisting of hydrogen, halogen, —R, —OR, —OSO$_2$CF$_3$, —OCOR, —SR, —NR$_2$, and —PR$_2$ groups, wherein the R substituents are linear or branched, saturated or unsaturated, C$_1$-C$_{20}$ alkyl, C$_3$-C$_{20}$ cycloalkyl, C$_6$-C$_{20}$ aryl, C$_7$-C$_{20}$ alkylaryl, or C$_7$-C$_{20}$ arylalkyl radicals, optionally containing one or more atoms belonging to groups 13-17 of the Periodic Table of the Elements, and two R substituents may form a 5-7 membered ring, preferably X is a C$_1$ to C$_{20}$ alkyl or halogen, such as chlorine, bromine, iodine, fluorine, methyl, ethyl, propyl, butyl, pentyl, hexyl, heptyl, octyl, nonyl, decyl, undecyl, dodecyl or an isomer thereof;

the L groups, the same or different from each other, are anionic leaving group ligands;

R$^1$, R$^2$, R$^3$, R$^4$, R$^5$, R$^6$, and R$^7$ are each independently a hydrogen atom or a substituted or unsubstituted C$_1$ to C$_{20}$ hydrocarbyl group, and, optionally, any two of R$^5$, R$^6$, and R$^7$ can be joined to form a cyclic structure (R$^1$, R$^2$, R$^3$, R$^4$, R$^5$, R$^6$, and R$^7$ are each independently a C$_1$ to C$_{20}$ alkyl, such as methyl, ethyl, propyl, butyl, pentyl, hexyl, heptyl, octyl, nonyl, decyl, undecyl, dodecyl, or an isomer thereof).

In another aspect in any embodiment of any formula described herein, the metal M is Zr or Hf.

In another aspect in any embodiment of any formula described herein, the X groups are Cl or Br.

In another aspect in any embodiment of any formula described herein, R$^2$ is a substituted or unsubstituted C$_1$ to C$_{20}$ hydrocarbyl group (such as linear branched or cyclic methyl, ethyl, propyl, butyl, pentyl, hexyl, heptyl, octyl, nonyl, decyl, undecyl, or dodecyl, or an isomer thereof, preferably methyl).

In another aspect in any embodiment of any formula described herein, R$^3$, R$^5$, R$^6$, and R$^7$ are each independently a hydrogen atom or a substituted or unsubstituted C$_1$ to C$_{20}$ hydrocarbyl group (such as linear branched or cyclic methyl, ethyl, propyl, butyl, pentyl, hexyl, heptyl, octyl, nonyl, decyl, undecyl, or dodecyl, or an isomer thereof), and, optionally, any two of R$^5$, R$^6$, and R$^7$ can be joined to form a cyclic structure.

In another aspect in any embodiment of any formula described herein, R$^4$ is a substituted or unsubstituted aryl group (such as phenyl or phenyl substituted at 1, 2, or 3 positions with one or more of methyl, ethyl, propyl, butyl, pentyl, hexyl, heptyl, octyl, nonyl, decyl, undecyl, dodecyl, phenyl, substituted phenyl, or an isomer thereof).

In another aspect in any embodiment of any formula described herein, R$^2$ is a substituted or unsubstituted C$_1$ to a C$_{20}$ hydrocarbyl group (such as methyl, ethyl, propyl, butyl, pentyl, hexyl, heptyl, octyl, nonyl, decyl, undecyl, dodecyl or an isomer thereof) and R$^4$ is a substituted or unsubstituted aryl group (such as phenyl or substituted phenyl, such as 3'5'di-t-butylphenyl).

In yet another aspect, in any embodiment of any formula described herein, the L groups are independently selected from the group consisting of: any leaving group; halogen ions, hydrides, hydrocarbyls, lower hydrocarbyls, substituted hydrocarbyls, heterohydrocarbyls, alkyls (lower alkyls, substituted alkyls, heteroalkyls), alkenyls (lower alkenyls, substituted alkenyls, heteroalkenyls), alkynyls (lower alkynyls, substituted alkynyls, heteroalkynyls), alkoxys (lower alkoxys), aryloxys, hydroxyls, alkylthios, lower alkyls thios, arylthios, thioxys, aryls (substituted aryls, heteroaryls), aralkyls, aralkylenes, alkaryls, alkarylenes, halides, haloalkyls, haloalkenyls, haloalkynyls, heteroalkyls, heterocycles, heteroaryls, heteroatom-containing groups, silyls, boryls, phosphinos, phosphines, aminos, amines, cycloalkyls, acyls, aroyls, alkylthiols, dialkylamines, alkylamidos, alkoxycarbonyls, aryloxycarbonyls, carbomoyls, alkyl- and dialkyl-carbamoyls, acyloxys, acylaminos, aroylaminos, and combinations thereof; alternately L is selected from C$_1$ to C$_{12}$ alkyls, C$_2$ to C$_{12}$ alkenyls, C$_6$ to C$_{12}$ aryls, C$_7$ to C$_{20}$ alkylaryls, C$_1$ to C$_{12}$ alkoxys, C$_6$ to C$_{16}$ aryloxys, C$_7$ to C$_{18}$ alkylaryloxys, C$_1$ to C$_{12}$ fluoroalkyls, C$_6$ to C$_{12}$ fluoroaryls, and C$_1$ to C$_{12}$ heteroatom-containing hydrocarbons and substituted derivatives thereof; alternately L is selected from hydride, halogen ions, C$_1$ to C$_6$ alkyls, C$_2$ to C$_6$ alkenyls, C$_7$ to C$_{18}$ alkylaryls, C$_1$ to C$_6$ alkoxys, C$_6$ to C$_{14}$ aryloxys, C$_7$ to C$_{16}$ alkylaryloxys, C$_1$ to C$_6$ alkylcarboxylates, C$_1$ to C$_6$ fluorinated alkylcarboxylates, C$_6$ to C$_{12}$ arylcarboxylates, C$_7$ to C$_{18}$ alkylarylcarboxylates, C$_1$ to C$_6$ fluoroalkyls, C$_2$ to C$_6$ fluoroalkenyls, and C$_7$ to C$_{18}$ fluoroalkylaryls; alternately L is selected from hydride, chloride, fluoride, methyl, phenyl, phenoxy, benzoxy, tosyl, fluoromethyls and fluorophenyls; alternately L is selected from C$_1$ to C$_{12}$ alkyls, C$_2$ to C$_{12}$ alkenyls, C$_6$ to C$_{12}$ aryls, C$_7$ to C$_{20}$ alkylaryls, substituted C$_1$ to C$_{12}$ alkyls, substituted C$_6$ to C$_{12}$ aryls, substituted C$_7$ to C$_{20}$ alkylaryls and C$_1$ to C$_{12}$ heteroatom-containing alkyls, C$_1$ to C$_{12}$ heteroatom-containing aryls and C$_1$ to C$_{12}$ heteroatom-containing alkylaryls; alternately L is selected from chloride, fluoride, C$_1$ to C$_6$ alkyls, C$_2$ to C$_6$ alkenyls, C$_7$ to C$_{18}$ alkylaryls, halogenated C$_1$ to C$_6$ alkyls, halogenated C$_2$ to C$_6$ alkenyls, and halogenated C$_7$ to C$_{18}$ alkylaryls; alternately L is selected from fluoride, methyl, ethyl, propyl, phenyl, methylphenyl, dimethylphenyl, trimethylphenyl, fluoromethyls (mono-, di- and trifluoromethyls) and fluorophenyls (mono-, di-, tri-, tetra- and pentafluorophenyls). Other non-limiting examples of L groups include amines, phosphines, ethers, carboxylates, dienes, hydrocarbon radicals having from 1 to 20 carbon atoms, fluorinated hydrocarbon radicals (e.g., —C$_6$F$_5$ (pentafluorophenyl)), fluorinated alkylcarboxylates (e.g., CF$_3$C(O)O—), hydrides and halogen ions and combinations thereof. Other examples of L ligands include alkyl groups such as cyclobutyl, cyclohexyl, methyl, heptyl, tolyl, trifluoromethyl, tetramethylene, pentamethylene, methylidene, methyoxy, ethyoxy, propoxy, phenoxy, bis(N-methylanilide), dimethylamide, dimethylphosphide radicals, and the like. In one embodiment, two or more L groups form a part of a fused ring or ring system.

It should be understood that any of the selections of substituents and groups noted above can be combined in any manner and are not limiting.

In a preferred embodiment of the invention, the complex of Formula (II) or (IV) is prepared at a yield of at least 50%, preferably at least 60%, preferably at least 70%, preferably at least 80%, preferably 88 to 100%.

Hydrogenation of the complex of Formula (I) or (III) can be accomplished using any hydrogenation catalyst. Preferably the hydrogenation catalyst is selected from the group consisting of supported Group 7, 8, 9, and 10 metals, preferably one or more of Ni, Pd, Pt, Co, Rh, Fe, Ru, Os, Cr, Mo, and W, optionally supported on silica, alumina, clay, titania, zirconia, or mixed metal oxide supports. A preferred hydrogenation catalyst is nickel supported on kieselguhr, or platinum or palladium supported on alumina, or cobalt-molydenum supported on alumina. Usually, a high nickel content catalyst, such as 60% Ni on Keiselguhr catalyst is used, or a supported catalyst with high a amount of Co—Mo loading. Particularly useful hydrogenation catalysts include PdO$_2$.

Preferably the complex of Formula (I) or (III) is contacted with hydrogen and a hydrogenation catalyst at a temperature from 100 to 300° C. for a time period from 5 minutes to 24 hours, and at a hydrogen pressure of from 100 to 2000 psi.

In a preferred embodiment of the invention, the complex of Formula (I) or (III) is contacted with hydrogen (preferably at a hydrogen pressure of from 25 psi to 2500 psi (0.17 MPa to 17.24 MPa), preferably from 100 to 2000 psi (0.69 MPa to 13.79 MPa)), and a hydrogenation catalyst at a temperature from 25° C. to 350° C., preferably 100° C. to 300° C., and/or a time period from 5 minutes to 100 hours, preferably from 5 minutes to 24 hours. The hydrogenation process can be accomplished in a slurry reactor in a batch operation or in a continuous stirred tank reactor (CSTR), where the catalyst, hydrogen, and the complex are continuously added to the reactor to allow for certain residence time, usually 5 minutes to 10 hours to allow complete hydrogenation of the unsaturated olefins. The amount of catalyst added is usually very small, for example, in 0.001 wt % to 20 wt % of the complex feed or preferably 0.01 wt % to 10 wt %, just to compensate for the catalyst deactivation. The catalyst and hydrogenated complex are continuously withdrawn from the reactor. The product mixture may then be filtered, centrifuged, or settled to remove the solid hydrogenation catalyst.

In the above reactions, the cyclopentadienyl ring bound to the metal does not hydrogenate because it is very stable as an aromatic group with strong bonds to the metal. The other ring is not as stable since it is not aromatic, so it is easier to hydrogenate.

Metallocene Production

In another embodiment, the present invention relates to a method for preparing a metallocene catalyst, comprising the steps of: (a) contacting a complex of Formula (I):

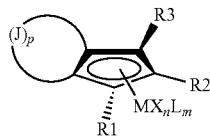

wherein: J, p, M, X, L, m, n, $R^1$, $R^2$ and $R^3$ are as described above; with hydrogen and a hydrogenation catalyst to obtain a complex of Formula (II):

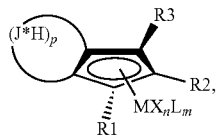
(II);

wherein: M, X, L, n, m, p, R, $R^1$, $R^2$, $R^3$, and J*; (b) are as described above and (b) reacting the complex of Formula (II) with a substituted or unsubstituted lithiated cyclopentadiene (Li-Cp) to prepare a metallocene catalyst of Formula (VI):

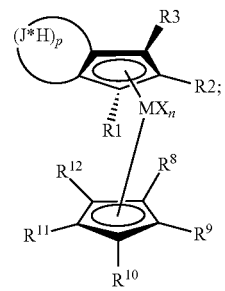
(VI)

wherein: M, X, n, p, $R^1$, $R^2$, $R^3$, and J*; (b) are as described above and $R^8$, $R^9$, $R^{10}$, $R^{11}$, and $R^{12}$, are independently as described for $R^1$.

In another embodiment, the present invention relates to a method for preparing a metallocene catalyst, comprising the steps of: (a) preparing a complex of Formula (III):

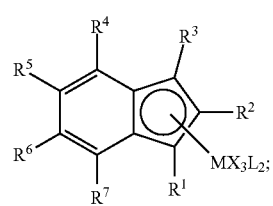
(III)

(b) reacting the complex of Formula (I) with hydrogen to prepare a complex of Formula (IV):

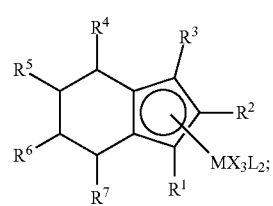
(IV)

and
(c) reacting the complex of Formula (IV) with lithiated substituted or unsubstituted cyclopentadiene (Li-Cp) to prepare a metallocene catalyst of Formula (V):

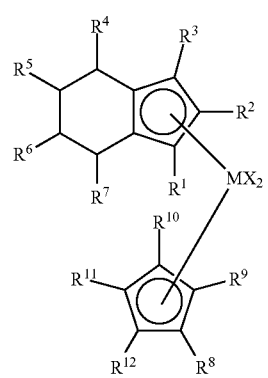
(V)

wherein: M is a transition metal belonging to group 3, 4, 5, 6 or to the lanthanide or actinide groups of the Periodic Table of the Elements (preferably Hf, Zr, or Ti);

the X groups, the same or different from each other, are monoanionic sigma ligands selected from the group consisting of hydrogen, halogen, —R, —OR, —OSO$_2$CF$_3$, —OCOR, —SR, —NR$_2$, and —PR$_2$ groups, wherein the R substituents are linear or branched, saturated or unsaturated, $C_1$-$C_{20}$ alkyl, $C_3$-$C_{20}$ cycloalkyl, $C_6$-$C_{20}$ aryl, $C_7$-$C_{20}$ alkylaryl, or $C_7$-$C_{20}$ arylalkyl radicals, optionally containing one or more atoms belonging to groups 13-17 of the Periodic Table of the Elements, and two R substituents may form a 5-7 membered ring, preferably X is a $C_1$ to $C_{20}$ alkyl or halogen, such as chlorine, bromine, iodine, fluorine, methyl, ethyl, propyl, butyl, pentyl, hexyl, heptyl, octyl, nonyl, decyl, undecyl, dodecyl or an isomer thereof;

the L groups, the same or different from each other, are anionic leaving group ligands;

$R^1$, $R^2$, $R^3$, $R^4$, $R^5$, $R^6$, $R^7$ $R^8$, $R^9$, $R^{10}$, $R^{11}$ and $R^{12}$, are each independently a hydrogen atom or a substituted or unsubstituted $C_1$ to $C_{20}$ hydrocarbyl group, and, optionally, any two of $R^5$, $R^6$, and $R^7$ can be joined to form a cyclic structure preferably X is a $C_1$ to $C_{20}$ alkyl, such as methyl, ethyl, propyl, butyl, pentyl, hexyl, heptyl, octyl, nonyl, decyl, undecyl, dodecyl or an isomer thereof, preferably, $R^2$ is a substituted or unsubstituted $C_1$ to $C_{20}$ hydrocarbyl group (such as methyl, ethyl, propyl, butyl, pentyl, hexyl, heptyl, octyl, nonyl, decyl, undecyl, dodecyl or an isomer thereof) and $R^4$ is a substituted or unsubstituted aryl group (such as phenyl or substituted phenyl); and $R^8$, $R^9$, $R^{10}$, $R^{11}$, and $R^{12}$ are each independently a substituted or unsubstituted $C_1$ to $C_6$ hydrocarbyl group (such as methyl, ethyl, propyl, butyl, pentyl, or hexyl) and any two of $R^8$, $R^9$, $R^{10}$, $R^{11}$, and $R^{12}$ adjacent to each other can be joined to form a cyclic structure.

Likewise, the complexes are formed, for example, from the anionic ligand and Zr(NMe$_2$)$_3$Cl to give the compound LZr(NMe$_2$)$_3$ (L=dihydropentalenyl, indenyl, dihydroazulenyl, bicycloundecapentaenyl, etc.), which is then reacted with Me$_3$SiCl in dme to give LZrCl$_3$(dme). After the previous compound is hydrogenated to (LH)ZrCl$_3$(dme), it is then reacted with LiCp (Cp=cyclopentadienyl, indenyl, fluorenyl, etc.) to give the metallocene Cp(LH)ZrCl$_2$.

In one aspect, in any embodiment of any catalyst or method described herein, the metal M is Zr or Hf.

In another aspect, in any embodiment of any formula or method described herein, the X groups are Cl or Br, and are preferably the same.

In yet another aspect, in any embodiment of any method or formula described herein, the L groups are independently selected from the group consisting of: any leaving group in one embodiment; halogen ions, hydrides, hydrocarbyls, lower hydrocarbyls, substituted hydrocarbyls, heterohydrocarbyls, alkyls (lower alkyls, substituted alkyls, heteroalkyls), alkenyls (lower alkenyls, substituted alkenyls, heteroalkenyls), alkynyls (lower alkynyls, substituted alkynyls, heteroalkynyls), alkoxys (lower alkoxys), aryloxys, hydroxyls, alkylthios, lower alkyls thios, arylthios, thioxys, aryls (substituted aryls, heteroaryls), aralkyls, aralkylenes, alkaryls, alkarylenes, halides, haloalkyls, haloalkenyls, haloalkynyls, heteroalkyls, heterocycles, heteroaryls, heteroatom-containing groups, silyls, boryls, phosphinos, phosphines, aminos, amines, cycloalkyls, acyls, aroyls, alkylthiols, dialkylamines, alkylamidos, alkoxycarbonyls, aryloxycarbonyls, carbomoyls, alkyl- and dialkyl-carbamoyls, acyloxys, acylaminos, aroylaminos, and combinations thereof in another embodiment; L is $C_1$ to $C_{12}$ alkyls, $C_2$ to $C_{12}$ alkenyls, $C_6$ to $C_{12}$ aryls, $C_7$ to $C_{20}$ alkylaryls, $C_1$ to $C_{12}$ alkoxys, $C_6$ to $C_{16}$ aryloxys, $C_7$ to $C_{18}$ alkylaryloxys, $C_1$ to $C_{12}$ fluoroalkyls, $C_6$ to $C_{12}$ fluoroaryls, and $C_1$ to $C_{12}$ heteroatom-containing hydrocarbons and substituted derivatives thereof in a more particular embodiment; hydride, halogen ions, $C_1$ to $C_6$ alkyls, $C_2$ to $C_6$ alkenyls, $C_7$ to $C_{18}$ alkylaryls, $C_1$ to $C_6$ alkoxys, $C_6$ to $C_{14}$ aryloxys, $C_7$ to $C_{16}$ alkylaryloxys, $C_1$ to $C_6$ alkylcarboxylates, $C_1$ to $C_6$ fluorinated alkylcarboxylates, $C_6$ to $C_{12}$ arylcarboxylates, $C_7$ to $C_{18}$ alkylarylcarboxylates, $C_1$ to $C_6$ fluoroalkyls, $C_2$ to $C_6$ fluoroalkenyls, and $C_7$ to $C_{18}$ fluoroalkylaryls in yet a more particular embodiment; hydride, chloride, fluoride, methyl, phenyl, phenoxy, benzoxy, tosyl, fluoromethyls and fluorophenyls in yet a more particular embodiment; $C_1$ to $C_{12}$ alkyls, $C_2$ to $C_{12}$ alkenyls, $C_6$ to $C_{12}$ aryls, $C_7$ to $C_{20}$ alkylaryls, substituted $C_1$ to $C_{12}$ alkyls, substituted $C_6$ to $C_{12}$ aryls, substituted $C_7$ to $C_{20}$ alkylaryls and $C_1$ to $C_{12}$ heteroatom-containing alkyls, $C_1$ to $C_{12}$ heteroatom-containing aryls and $C_1$ to $C_{12}$ heteroatom-containing alkylaryls in yet a more particular embodiment; chloride, fluoride, $C_1$ to $C_6$ alkyls, $C_2$ to $C_6$ alkenyls, $C_7$ to $C_{18}$ alkylaryls, halogenated $C_1$ to $C_6$ alkyls, halogenated $C_2$ to $C_6$ alkenyls, and halogenated $C_7$ to $C_{18}$ alkylaryls in yet a more particular embodiment; fluoride, methyl, ethyl, propyl, phenyl, methylphenyl, dimethylphenyl, trimethylphenyl, fluoromethyls (mono-, di- and trifluoromethyls) and fluorophenyls (mono-, di-, tri-, tetra- and pentafluorophenyls) in yet a more particular embodiment. Other non-limiting examples of L groups include amines, phosphines, ethers, carboxylates, dienes, hydrocarbon radicals having from 1 to 20 carbon atoms, fluorinated hydrocarbon radicals (e.g., —C$_6$F$_5$ (pentafluorophenyl)), fluorinated alkylcarboxylates (e.g., CF$_3$C(O)O—), hydrides and halogen ions and combinations thereof. Other examples of L ligands include alkyl groups such as cyclobutyl, cyclohexyl, methyl, heptyl, tolyl, trifluoromethyl, tetramethylene, pentamethylene, methylidene, methyoxy, ethyoxy, propoxy, phenoxy, bis(N-methylanilide), dimethylamide, dimethylphosphide radicals, and the like. In one embodiment, two or more L groups form a part of a fused ring or ring system.

In still yet another aspect, in any embodiment of any method or formula described herein, $R^2$ is a primary substituted or unsubstituted $C_1$-$C_{12}$ alkyl group. Preferably, $R^2$ is methyl, ethyl, or n-propyl.

In another aspect, in any embodiment of any method or formula described herein, $R^4$ is selected from an aryl group, such as phenyl, 1-naphthyl, 2-naphthyl, 9-anthracenyl, 2-biphenyl, 3-biphenyl, 4-biphenyl, 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,5-trimethylphenyl, 3,4,5-trimethylphenyl, 2,3,4,5,6-pentamethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 3,5-diethylphenyl, 3-isopropylphenyl, 4-isopropylphenyl, 3,5-diisopropylphenyl, 2,5-di-isopropylphenyl, 2-tert-butylphenyl, 3-tert-butylphenyl, 4-tert-butylphenyl, 3,5-di-tert-butylphenyl, 2,5-di-tert-butylphenyl, 2-trimethylsilylphenyl, 3-trimethylsilylphenyl, 4-trimethylsilylphenyl, 3,5-bis(trimethylsilyl)phenyl, 2-trifluoromethylphenyl, 3-trifluoromethylphenyl, 4-trifluoromethylphenyl, 3,5-bis(trifluoromethyl)phenyl, cyclopropyl, carbazolyl, indolyl, pyrrolyl, or 2-furanyl, 3-furanyl, 5-methyl-2-furanyl, 5-ethyl-2-furanyl, 4,5-dimethyl-2-furanyl, 2-methyl-3-furanyl, 5-methyl-3-furanyl, 2-thiophenyl, 3-thiophenyl, 5-methyl-2-thiophenyl, 2-methyl-3-thiophenyl, or 5-methyl- 3-thiophenyl. Examples of useful aryl groups include phenyl, benzyl, carbazolyl, naphthyl, and the like.

In still yet another aspect, in any embodiment of any method or formula described herein, $R^3$ is a hydrogen atom.

In yet another aspect, in any embodiment of any method or formula described herein, $R^5$, $R^6$, and $R^7$ are independently a hydrogen atom or a substituted or unsubstituted $C_1$ to $C_6$ hydrocarbyl group, and any two of $R^5$, $R^6$, and $R^7$ can be joined to form a cyclic structure.

In yet another aspect, in any embodiment of any method or formula described herein, $R^1$, $R^8$, $R^9$, $R^{10}$, $R^{11}$ and $R^{12}$, are independently a hydrogen atom or a substituted or unsubstituted $C_1$ to a $C_6$ hydrocarbyl group, and any two of $R^1$, $R^8$, $R^9$, $R^{10}$, $R^{11}$ and $R^{12}$ can be joined to form a cyclic structure.

It has been surprisingly discovered that tetrahydroindenyl metal complexes of the type $(H_4Ind)MX_3L_2$ can be conveniently and efficiently formed by hydrogenation of corresponding indenyl metal complexes, which can be qualified as a desired candidate to replace the conventional ineffective route for preparing tetrahydroindenyl metal complexes starting from lithium tetrahydroindenide complexes, thus broadening the available selection of synthesis routes for relevant metallocene catalysts.

In embodiments, the metallocene compounds described herein may be "asymmetric," meaning that they have no planes of symmetry. An asymmetric catalyst according to this invention is a metallocene compound comprising at least two organic ligands which differ in their chemical structure. Still more preferably, the asymmetric catalyst, according to this invention, is a metallocene compound comprising at least two organic ligands which differ in their chemical structure and the metallocene compound is free of $C_2$-symmetry and/or any higher symmetry (one or more planes of symmetry). Preferably, the asymmetric metallocene compound, comprises only two different organic ligands, still more preferably comprises two organic ligands which are different and linked via a bridge. A ligand is considered different from another ligand if they differ by at least one atom. For example, "indenyl" is different from "2-methylindenyl."

In a preferred embodiment, metallocene compounds prepared according to the method in the present invention may include: cyclopentadienyl(1-methyl-4,5,6,7-tetrahydroindenyl)zirconium dichloride, cyclopentadienyl(1-ethyl-4,5,6,7-tetrahydroindenyl)zirconium dichloride, cyclopentadienyl(1-t-butyl-4,5,6,7-tetrahydroindenyl)zirconium dichloride, cyclopentadienyl(1-phenyl-4,5,6,7-tetrahydroindenyl)zirconium dichloride, cyclopentadienyl(1,3-dimethyl-4,5,6,7-tetrahydroindenyl)zirconium dichloride, cyclopentadienyl(4,7-dimethyl-4,5,6,7-tetrahydroindenyl)zirconium dichloride, cyclopentadienyl(4-phenyl-4,5,6,7-tetrahydroindenyl)zirconium dichloride, cyclopentadienyl(4-terbutyl-7-methyl-4,5,6,7-tetrahydroindenyl)zirconium dichloride, the corresponding zirconium dibromide metallocenes, and mixtures thereof.

Non-limiting examples of metallocene compounds prepared according to the method in the present invention may also include: (2,3,4,5-tetramethyl-1-cyclopentadienyl)(2-methyl-4-phenyl-4,5,6,7-tetrahydroindenyl)titanium dichloride, (2,3,4,5-tetramethyl-1-cyclopentadienyl)(2-methyl-4-phenyl-4,5,6,7-tetrahydroindenyl)zirconium dichloride, (2,3,4,5-tetramethyl-1-cyclopentadienyl)(2-methyl-4-phenyl-4,5,6,7-tetrahydroindenyl)hafnium dichloride, (2,3,4,5-tetramethyl-1-cyclopentadienyl)(2-methyl-4-phenyl-4,5,6,7-tetrahydroindenyl)zirconium dibromide, (2,3,4,5-tetramethyl-1-cyclopentadienyl)(2-methyl-4-phenyl-4,5,6,7-tetrahydroindenyl)zirconium diiodide, (2,3,4,5-tetramethyl-1-cyclopentadienyl)(2-methyl-4-phenyl-4,5,6,7-tetrahydroindenyl)zirconium dimethoxide, (2,3,4,5-tetramethyl-1-cyclopentadienyl)(2-methyl-4-phenyl-4,5,6,7-tetrahydroindenyl)zirconium diethoxide, (2,3,4,5-tetramethyl-1-cyclopentadienyl)(2-methyl-4-phenyl-4,5,6,7-tetrahydroindenyl)zirconium diisopropoxide, (2,3,4,5-tetramethyl-1-cyclopentadienyl)(2-methyl-4-phenyl-4,5,6,7-tetrahydroindenyl)zirconium di-t-butoxide, (2,3,4,5-tetramethyl-1-cyclopentadienyl)(2-methyl-4-phenyl-4,5,6,7-tetrahydroindenyl)zirconium bis(dimethylamide), (2,3,4,5-tetramethyl-1-cyclopentadienyl)(2-methyl-4-phenyl-4,5,6,7-tetrahydroindenyl)zirconium bis(diethylamide), (2,3,4,5-tetramethyl-1-cyclopentadienyl)(2-methyl-4-phenyl-4,5,6,7-tetrahydroindenyl)zirconium bis(diisopropylamide), (2,3,4,5-tetramethyl-1-cyclopentadienyl)(2-methyl-4-phenyl-4,5,6,7-tetrahydroindenyl)zirconium bis(trifluoromethanesulfonate), (2,3,4,5-tetramethyl-1-cyclopentadienyl)(2-methyl-4-phenyl-4,5,6,7-tetrahydroindenyl)zirconium bis(p-toluenesulfonate), (2,3,4,5-tetramethyl-1-cyclopentadienyl)(2-methyl-4-phenyl-4,5,6,7-tetrahydroindenyl)zirconiumdimethyl, (2,3,4,5-tetramethyl-1-cyclopentadienyl)(2-methyl-4-phenyl-4,5,6,7-tetrahydroindenyl)zirconiumdiethyl, (2,3,4,5-tetramethyl-1-cyclopentadienyl)(2-methyl-4-phenyl-4,5,6,7-tetrahydroindenyl)zirconiumdibenzyl, (2,3,4,5-tetramethyl-1-cyclopentadienyl)(2-methyl-4-phenyl-4,5,6,7-tetrahydroindenyl)zirconiumdiphenyl, (2,3,4,5-tetraethyl-1-cyclopentadienyl)(2-methyl-4-phenyl-4,5,6,7-tetrahydroindenyl)zirconium dichloride, (2,3,4,5-tetrapropyl-1-cyclopentadienyl)(2-methyl-4-phenyl-4,5,6,7-tetrahydroindenyl)zirconium dichloride, (3,4-dimethyl-1-cyclopentadienyl)(2-methyl-4-phenyl-4,5,6,7-tetrahydroindenyl)zirconium dichloride, (3,4-di ethyl-1-cyclopentadienyl)(2-methyl-4-phenyl-4,5,6,7-tetrahydroindenyl)zirconium dichloride, (2-indenyl)(2-methyl-4-phenyl-4,5,6,7-tetrahydroindenyl)zirconium dichloride, (1,3-dimethyl-2-indenyl)(2-methyl-4-phenyl-4,5,6,7-tetrahydroindenyl)zirconium dichloride, (2,3,4,5-tetramethyl-1-cyclopentadienyl)(2, 3-dimethyl-4-phenyl-4,5,6,7-tetrahydroindenyl)zirconium dichloride, (2,3,4,5-tetramethyl-1-cyclopentadienyl)(2,5-dimethyl-4-phenyl-4,5,6,7-tetrahydroindenyl)zirconium dichloride, (2,3,4,5-tetramethyl-1-cyclopentadienyl)(2,5,6-trimethyl-4-phenyl-4,5,6,7-tetrahydroindenyl)zirconium dichloride, (2,3,4,5-tetramethyl-1-cyclopentadienyl)(2-methyl-4-phenyl-benz[f]-4,5,6,7-tetrahydroindenyl)zirconium dichloride, (2,3,4,5-tetramethyl-1-cyclopentadienyl)(2-methyl-4-phenyl-benz[e]-4,5,6,7-tetrahydroindenyl)zirconium dichloride, (2,3,4,5-tetramethyl-1-cyclopentadienyl)(2-ethyl-4-phenyl-4,5,6,7-tetrahydroindenyl)zirconium dichloride, (2,3,4,5-tetramethyl-1-cyclopentadienyl)(2-propyl-4-phenyl-4,5,6,7-tetrahydroindenyl)zirconium dichloride, (2,3,4,5-tetramethyl-1-cyclopentadienyl)(2-isobutyl-4-phenyl-4,5,6,7-tetrahydroindenyl)zirconium dichloride, (2,3,4,5-tetramethyl-1-cyclopentadienyl)(2-neopentyl-4-phenyl-4,5,6,7-tetrahydroindenyl)zirconium dichloride, (2,3,4,5-tetramethyl-1-cyclopentadienyl)(2-cyclohexylmethyl-4-phenyl-4,5,6,7-tetrahydroindenyl)zirconium dichloride, (2,3,4,5-tetramethyl-1-cyclopentadienyl)(2-cyclopropyl-4-phenyl-4,5,6,7-tetrahydroindenyl)zirconium dichloride, (2,3,4,5-tetramethyl-1-cyclopentadienyl)(2-methyl-4-(2-methyl)phenyl)-4,5,6,7-tetrahydroindenyl)zirconium dichloride, (2,3,4,5-tetramethyl-1-cyclopentadienyl)(2-methyl-4-(3-methyl)phenyl)-4,5,6,7-tetrahydroindenyl)zirconium dichloride, (2,3,4,5-tetramethyl-1-cyclopentadienyl)(2-methyl-4-(4-methyl)phenyl)-4,5,6,7-tetrahydroindenyl)

zirconium dichloride, (2,3,4,5-tetramethyl-1-cyclopentadienyl)(2-methyl-4-(3,5-dimethyl)phenyl)-4,5,6,7-tetrahydroindenyl)zirconium dichloride, (2,3,4,5-tetramethyl-1-cyclopentadienyl)(2-methyl-4-(3,4,5-trimethyl)phenyl)-4,5,6,7-tetrahydroindenyl)zirconium dichloride, (2,3,4,5-tetramethyl-1-cyclopentadienyl)(2-methyl-4-(4-t-butyl)phenyl)-4,5,6,7-tetrahydroindenyl)zirconium dichloride, (2,3,4,5-tetramethyl-1-cyclopentadienyl)(2-methyl-4-(3,5-di-t-butyl)phenyl)-4,5,6,7-tetrahydroindenyl)zirconium dichloride, (2,3,4,5-tetramethyl-1-cyclopentadienyl)(2-methyl-4-(1-naphthyl)-4,5,6,7-tetrahydroindenyl)zirconium dichloride, (2,3,4,5-tetramethyl-1-cyclopentadienyl)(2-methyl-4-(2-naphthyl)-4,5,6,7-tetrahydroindenyl)zirconium dichloride, (2,3,4,5-tetramethyl-1-cyclopentadienyl)(2-methyl-4-(2-biphenyl)-4,5,6,7-tetrahydroindenyl)zirconium dichloride, (2,3,4,5-tetramethyl-1-cyclopentadienyl)(2-methyl-4-(3-biphenyl)-4,5,6,7-tetrahydroindenyl)zirconium dichloride, (2,3,4,5-tetramethyl-1-cyclopentadienyl)(2-methyl-4-(4-biphenyl)-4,5,6,7-tetrahydroindenyl)zirconium dichloride, (2,3,4,5-tetramethyl-1-cyclopentadienyl)(2-methyl-4-(4-trifluoromethylphenyl)-4,5,6,7-tetrahydroindenyl)zirconium dichloride, (2,3,4,5-tetramethyl-1-cyclopentadienyl)(2-methyl-4-(3,5-bis(trifluoromethy]phenyl)-4,5,6,7-tetrahydroindenyl)zirconium dichloride, (2,3,4,5-tetramethyl-1-cyclopentadienyl)(2-methyl-4-(2-furanyl)-4,5,6,7-tetrahydroindenyl)zirconium dichloride, (2,3,4,5-tetramethyl-1-cyclopentadienyl)(2-methyl-4-(5-methyl-2-furanyl)-4,5,6,7-tetrahydroindenyl)zirconium dichloride, (2,3,4,5-tetramethyl-1-cyclopentadienyl)(2-methyl-4-(5-ethyl-2-furanyl)-4,5,6,7-tetrahydroindenyl)zirconium dichloride, (2,3,4,5-tetramethyl-1-cyclopentadienyl)(2-methyl-4-(2-thiophenyl)-4,5,6,7-tetrahydroindenyl)zirconium dichloride, (2,3,4,5-tetramethyl-1-cyclopentadienyl)(2-methyl-4-(5-methyl-2-thiophenyl)-4,5,6,7-tetrahydroindenyl)zirconium dichloride, and mixtures thereof.

Activators

The method for making the metallocene catalysts described herein may further comprise the step of combining the metallocene catalyst with an activator to prepare a catalyst system. The terms "cocatalyst" and "activator" are used herein interchangeably and are defined to be any compound which can activate any one of the catalyst compounds described above by converting the neutral catalyst compound to a catalytically active catalyst compound cation. Non-limiting activators, for example, include alumoxanes, aluminum alkyls, ionizing activators, which may be neutral or ionic, and conventional-type cocatalysts. Preferred activators typically include alumoxane compounds, modified alumoxane compounds, and ionizing anion precursor compounds that abstract a reactive, σ-bound, metal ligand making the metal complex cationic and providing a charge-balancing, non-coordinating anion or weakly coordinating anion.

In one embodiment, alumoxane activators are utilized as an activator in the catalyst composition. Alumoxanes are generally oligomeric compounds containing —Al(R$^1$)—O— sub-units, where R$^1$ is an alkyl group. Examples of alumoxanes include methylalumoxane (MAO), modified methylalumoxane (MMAO), ethylalumoxane, and isobutylalumoxane. Alkylalumoxanes and modified alkylalumoxanes are suitable as catalyst activators, particularly when the abstractable ligand is an alkyl, halide, alkoxide, or amide. Mixtures of different alumoxanes and modified alumoxanes may also be used. It may be preferable to use a visually clear methylalumoxane. A cloudy or gelled alumoxane can be filtered to produce a clear solution or clear alumoxane can be decanted from the cloudy solution. A useful alumoxane is a modified methyl alumoxane (MMAO) cocatalyst type 3A (commercially available from Akzo Chemicals, Inc. under the trade name Modified Methylalumoxane type 3A, covered under U.S. Pat. No. 5,041,584).

When the activator is an alumoxane (modified or unmodified), some embodiments select the maximum amount of activator typically at up to a 5000 fold molar excess Al/M over the catalyst compound (per metal catalytic site). The minimum activator to catalyst compound is a 1:1 molar ratio. Alternate preferred ranges include from 1:1 to 500:1, alternately from 1:1 to 200:1, alternately from 1:1 to 100:1, or alternately from 1:1 to 50:1.

In an alternate embodiment, little or no alumoxane is used in the polymerization processes described herein. Alternately, alumoxane is present at zero mol %, alternately the alumoxane is present at a molar ratio of aluminum to catalyst compound transition metal less than 500:1, preferably less than 300:1, preferably less than 100:1, preferably less than 1:1.

The term "non-coordinating anion" (NCA) means an anion which either does not coordinate to a cation or which is only weakly coordinated to a cation thereby remaining sufficiently labile to be displaced by a neutral Lewis base. "Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the transition metal cation in the sense of balancing its ionic charge at +1, and yet retain sufficient lability to permit displacement during polymerization.

It is within the scope of this invention to use an ionizing or stoichiometric activator, neutral or ionic, such as tri (n-butyl) ammonium tetrakis (pentafluorophenyl) borate, a tris perfluorophenyl boron metalloid precursor or a tris perfluoronaphthyl boron metalloid precursor, polyhalogenated heteroborane anions (WO 98/43983), boric acid (U.S. Pat. No. 5,942,459), or combinations thereof. It is also within the scope of this invention to use neutral or ionic activators alone or in combination with alumoxane or modified alumoxane activators.

Examples of neutral stoichiometric activators include tri-substituted boron, tellurium, aluminum, gallium, and indium, or mixtures thereof. The three substituent groups are each independently selected from alkyls, alkenyls, halogens, substituted alkyls, aryls, arylhalides, alkoxy, and halides. Preferably, the three groups are independently selected from halogen, mono, or multicyclic (including halosubstituted) aryls, alkyls, and alkenyl compounds, and mixtures thereof, preferred are alkenyl groups having 1 to 20 carbon atoms, alkyl groups having 1 to 20 carbon atoms, alkoxy groups having 1 to 20 carbon atoms, and aryl groups having 3 to 20 carbon atoms (including substituted aryls). More preferably, the three groups are alkyls having 1 to 4 carbon groups, phenyl, naphthyl, or mixtures thereof. Even more preferably, the three groups are halogenated, preferably fluorinated, aryl groups. A preferred neutral stoichiometric activator is tris perfluorophenyl boron or tris perfluoronaphthyl boron.

Ionic stoichiometric activator compounds may contain an active proton, or some other cation associated with, but not coordinated to, or only loosely coordinated to, the remaining ion of the ionizing compound. Such compounds and the like are described in European publications EP 0 570 982 A; EP 0 520 732 A; EP 0 495 375 A; EP 0 500 944 B1; EP 0 277 003 A; EP 0 277 004 A; U.S. Pat. No. 5,153,157; U.S. Pat. No. 5,198,401; U.S. Pat. No. 5,066,741; U.S. Pat. No. 5,206,197; U.S. Pat. No. 5,241,025; U.S. Pat. No. 5,384,299; U.S. Pat. No. 5,502,124; and U.S. Ser. No. 08/285,380, filed Aug. 3, 1994; all of which are fully incorporated herein by reference.

Preferred compounds useful as an activator in the process of this invention comprise a cation, which is preferably a Bronsted acid capable of donating a proton, and a compatible non-coordinating anion which anion is relatively large (bulky), capable of stabilizing the active catalyst species (the Group 4 cation), which is formed when the two compounds are combined and said anion will be sufficiently labile to be displaced by olefinic, diolefinic, and acetylenically unsaturated substrates or other neutral Lewis bases, such as ethers, amines, and the like. Two classes of useful compatible non-coordinating anions have been disclosed in EP 0 277 003 A1, and EP 0 277 004 A1: 1) anionic coordination complexes comprising a plurality of lipophilic radicals covalently coordinated to and shielding a central charge-bearing metal or metalloid core; and 2) anions comprising a plurality of boron atoms such as carboranes, metallacarboranes, and boranes.

In a preferred embodiment, the stoichiometric activators include a cation and an anion component, and are preferably represented by the following Formula (IV):

$$(Z)_d^+(A^{d-}) \qquad (IV)$$

wherein: Z is (L-H) or a reducible Lewis Acid, L is a neutral Lewis base; H is hydrogen; (L-H)$^+$ is a Bronsted acid; A$^{d-}$ is a non-coordinating anion having the charge d−; and d is an integer from 1 to 3.

When Z is (L-H) such that the cation component is (L-H)$_d^+$, the cation component may include Bronsted acids such as protonated Lewis bases capable of protonating a moiety, such as an alkyl or aryl, from the bulky ligand metallocene containing transition metal catalyst precursor, resulting in a cationic transition metal species. Preferably, the activating cation (L-H)$_d^+$ is a Bronsted acid, capable of donating a proton to the transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers, such as dimethyl ether diethyl ether, tetrahydrofuran, and dioxane, sulfoniums from thioethers, such as diethyl thioethers and tetrahydrothiophene, and mixtures thereof.

When Z is a reducible Lewis acid it is preferably represented by the formula: (Ar$_3$C$^+$), where Ar is aryl or aryl substituted with a heteroatom, a C$_1$ to C$_{40}$ hydrocarbyl, or a substituted C$_1$ to C$_{40}$ hydrocarbyl, preferably the reducible Lewis acid is represented by the formula: (Ph$_3$C$^+$), where Ph is phenyl or phenyl substituted with a heteroatom, a C$_1$ to C$_{40}$ hydrocarbyl, or a substituted C$_1$ to C$_{40}$ hydrocarbyl. In a preferred embodiment, the reducible Lewis acid is triphenyl carbenium.

The anion component A$^{d-}$ include those having the formula [M$^{k+}$Q$_n$]$^{d-}$ wherein k is 1, 2, or 3; n is 1, 2, 3, 4, 5, or 6, preferably 3, 4, 5, or 6; n−k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide, and two Q groups may form a ring structure. Preferably, each Q is a fluorinated hydrocarbyl group having 1 to 20 carbon atoms, more preferably each Q is a fluorinated aryl group, and most preferably each Q is a pentafluoryl aryl group. Examples of suitable Ad-components also include diboron compounds as disclosed in U.S. Pat. No. 5,447,895, which is fully incorporated herein by reference.

In a preferred embodiment, this invention relates to a process for polymerizing olefins comprising contacting olefins (preferably ethylene and or propylene) with the catalyst, an optional chain transfer agent and a boron-containing NCA activator represented by the Formula (V):

$$Z_d^+(A^{d-}) \qquad (V)$$

wherein: Z is (L-H) or a reducible Lewis acid; L is a neutral Lewis base (as further described above); H is hydrogen; (L-H) is a Bronsted acid (as further described above); A$^{d-}$ is a boron-containing, non-coordinating anion having the charge d− (as further described above); and d is 1, 2, or 3.

In a preferred embodiment in any NCA's represented by Formula (V) described above, the reducible Lewis acid is represented by the formula: (Ar$_3$C$^+$), where Ar is aryl or aryl substituted with a heteroatom, a C$_1$ to C$_{40}$ hydrocarbyl, or a substituted C$_1$ to C$_{40}$ hydrocarbyl, preferably the reducible Lewis acid is represented by the formula: (Ph$_3$C$^+$), where Ph is phenyl or phenyl substituted with a heteroatom, a C$_1$ to C$_{40}$ hydrocarbyl, or a substituted C$_1$ to C$_{40}$ hydrocarbyl.

In a preferred embodiment in any of the NCA's represented by Formula (V) described above, Z$_d^+$ is represented by the formula: (L-H)$_d^+$, wherein L is a neutral Lewis base; H is hydrogen; (L-H) is a Bronsted acid; and d is 1, 2, or 3, preferably (L-H)$_d^+$ is a Bronsted acid selected from ammoniums, oxoniums, phosphoniums, silyliums, and mixtures thereof.

In a preferred embodiment in any of the NCA's represented by Formula V described above, the anion component A$^{d-}$ is represented by the formula [M*$^{k*}$+Q*$_{n*}$]$^{d*-}$ wherein k* is 1, 2, or 3; n* is 1, 2, 3, 4, 5, or 6 (preferably 1, 2, 3, or 4); n*−k*=d*; M* is boron; and Q* is independently selected from hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q* having up to 20 carbon atoms with the proviso that in not more than 1 occurrence is Q* a halide.

This invention also relates to a method to polymerize olefins comprising contacting olefins (such as ethylene and or propylene) with the catalyst prepared as described herein, an optional chain transfer agent and an NCA activator represented by the Formula (VI):

$$R_nM^{**}(ArNHal)_{4-n} \qquad (VI);$$

wherein: R is a monoanionic ligand; M** is a Group 13 metal or metalloid; ArNHal is a halogenated, nitrogen-containing aromatic ring, polycyclic aromatic ring, or aromatic ring assembly in which two or more rings (or fused ring systems) are joined directly to one another or together; and n is 0, 1, 2, or 3. Typically, the NCA comprising an anion of Formula (VI) also comprises a suitable cation that is essentially non-interfering with the ionic catalyst complexes formed with the transition metal compounds, preferably the cation is Z$_d^+$ as described above.

In a preferred embodiment in any of the NCA's comprising an anion represented by Formula (VI) described above, R is selected from the group consisting of substituted or unsubstituted $C_1$ to $C_{30}$ hydrocarbyl aliphatic or aromatic groups, where substituted means that at least one hydrogen on a carbon atom is replaced with a hydrocarbyl, halide, halocarbyl, hydrocarbyl or halocarbyl substituted organometalloid, dialkylamido, alkoxy, aryloxy, alkysulfido, arylsulfido, alkylphosphido, arylphosphide, or other anionic substituent; fluoride; bulky alkoxides, where bulky means $C_4$ to $C_{20}$ hydrocarbyl groups; —$SR^1$, —$NR^2{}_2$, and —$PR^3{}_2$, where each $R^1$, $R^2$, or $R^3$ is independently a substituted or unsubstituted hydrocarbyl as defined above; or a $C_1$ to $C_{30}$ hydrocarbyl substituted organometalloid.

In a preferred embodiment in any of the NCA's comprising an anion represented by Formula (VI) described above, the NCA also comprises a cation comprising a reducible Lewis acid represented by the formula: ($Ar_3C^+$), where Ar is aryl or aryl substituted with a heteroatom, a $C_1$ to $C_{40}$ hydrocarbyl, or a substituted $C_1$ to $C_{40}$ hydrocarbyl, preferably the reducible Lewis acid represented by the formula: ($Ph_3C^+$), where Ph is phenyl or phenyl substituted with a heteroatom, a $C_1$ to $C_{40}$ hydrocarbyl, or a substituted $C_1$ to $C_{40}$ hydrocarbyl.

In a preferred embodiment in any of the NCA's comprising an anion represented by Formula (VI) described above, the NCA also comprises a cation represented by the formula: $(L-H)_d{}^+$, wherein L is a neutral Lewis base; H is hydrogen; (L-H) is a Bronsted acid; and d is 1, 2, or 3, preferably $(L-H)_d{}^+$ is a Bronsted acid selected from ammoniums, oxoniums, phosphoniums, silyliums, and mixtures thereof.

Further examples of useful activators include those disclosed in U.S. Pat. No. 7,297,653 and U.S. Pat. No. 7,799,879.

In a preferred embodiment of the invention, activators useful herein include: trimethylammonium tetrakis(perfluoronaphthyl)borate, N,N-dimethylanilinium tetrakis(perfluoronaphthyl)borate, N,N-diethylanilinium tetrakis(perfluoronaphthyl)borate, triphenylcarbenium tetrakis(perfluoronaphthyl)borate, trimethylammonium tetrakis(perfluorobiphenyl)borate, N,N-dimethylanilinium tetrakis(perfluorobiphenyl)borate, triphenylcarbenium tetrakis(perfluorobiphenyl)borate, and the types disclosed in U.S. Pat. No. 7,297,653, which is fully incorporated herein by reference.

In a preferred embodiment of the invention, activators useful herein include: N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, $[Ph_3C^+][B(C_6F_5)_4{}^-]$, $[Me_3NH^+][B(C_6F_5)_4{}^-]$, 1-(4-(tris(pentafluorophenyl)borate)-2,3,5,6-tetrafluorophenyl)pyrrolidinium, and tetrakis(pentafluorophenyl)borate, 4 (tris(pentafluorophenyl)borate)-2,3,5,6-tetrafluoropyridine.

In an embodiment of the invention, the activator comprises a triaryl carbonium (such as triphenylcarbenium tetraphenylborate, triphenylcarbenium tetrakis(pentafluorophenyl)borate, triphenylcarbenium tetrakis-(2,3,4,6-tetrafluorophenyl)borate, triphenylcarbenium tetrakis(perfluoronaphthyl)borate, triphenylcarbenium tetrakis(perfluorobiphenyl)borate, and triphenylcarbenium tetrakis(3,5-bis(trifluoromethyl)phenyl)borate).

Optional Scavengers or Co-Activators

In addition to these activator compounds, scavengers or co-activators may be used. Aluminum alkyl or organoaluminum compounds, which may be utilized as scavengers or co-activators include, for example, trimethylaluminum, triethylaluminum, triisobutylaluminum, tri-n-hexylaluminum, tri-n-octylaluminum, and diethyl zinc.

Optional Support Materials

In embodiments herein, the catalyst system may comprise an inert support material. Preferably, the supported material is a porous support material, for example, talc, and inorganic oxides. Other support materials include zeolites, clays, organoclays, or any other organic or inorganic support material and the like, or mixtures thereof.

Preferably, the support material is an inorganic oxide in a finely divided form. Suitable inorganic oxide materials for use in metallocene catalyst systems herein include Groups 2, 4, 13, and 14 metal oxides, such as silica, alumina, and mixtures thereof. Other inorganic oxides that may be employed, either alone or in combination with the silica, or alumina are magnesia, titania, zirconia, and the like. Other suitable support materials, however, can be employed, for example, finely divided functionalized polyolefins, such as finely divided polyethylene. Particularly useful supports include magnesia, titania, zirconia, montmorillonite, phyllosilicate, zeolites, talc, clays, and the like. Also, combinations of these support materials may be used, for example, silica-chromium, silica-alumina, silica-titania, and the like. Preferred support materials include $Al_2O_3$, $ZrO_2$, $SiO_2$, and combinations thereof, more preferably $SiO_2$, $Al_2O_3$, or $SiO_2/Al_2O_3$.

It is preferred that the support material, most preferably an inorganic oxide, has a surface area in the range of from about 10 to about 700 $m^2/g$, pore volume in the range of from about 0.1 to about 4.0 cc/g and average particle size in the range of from about 5 to about 500 μm. More preferably, the surface area of the support material is in the range of from about 50 to about 500 $m^2/g$, pore volume of from about 0.5 to about 3.5 cc/g and average particle size of from about 10 to about 200 μm. Most preferably, the surface area of the support material is in the range is from about 100 to about 400 $m^2/g$, pore volume from about 0.8 to about 3.0 cc/g and average particle size is from about 5 to about 100 μm. The average pore size of the support material useful in the invention is in the range of from 10 to 1000 Å, preferably 50 to about 500 Å, and most preferably 75 to about 350 Å. In some embodiments, the support material is a high surface area, amorphous silica (surface area=300 $m^2/gm$; pore volume of 1.65 $cm^3/gm$).

The support material should be dry, that is, free of absorbed water. Drying of the support material can be effected by heating or calcining at about 150° C. to about 1000° C., preferably at least about 200° C. When the support material is silica, it is heated to at least 200° C., preferably about 200° C. to about 850° C., and most preferably at about 600° C.; and for a time of about 1 minute to about 100 hours, from about 12 hours to about 72 hours, or from about 24 hours to about 60 hours. The calcined support material must have at least some reactive hydroxyl (OH) groups to produce supported catalyst systems of this invention. The calcined support material is then contacted with at least one polymerization catalyst comprising at least one metallocene compound and an activator.

The support material, having reactive surface groups, typically hydroxyl groups, is slurried in a non-polar solvent and the resulting slurry is contacted with a solution of a metallocene compound and an activator. In some embodiments, the slurry of the support material is first contacted with the activator for a period of time in the range of from about 0.1 hour to about 24 hours, from about 2 hours to about 16 hours, or from about 4 hours to about 8 hours. The solution of the metallocene compound is then contacted with the isolated support/activator. In some embodiments, the supported catalyst system is generated in situ. In an alternate embodiment, the slurry of the support material is first contacted with the catalyst compound for a period of time in the range of from about 0.1 hour to about 24 hours, from about 2 hours to about 16 hours, or from about 4 hours to about 8 hours. The slurry of the supported metallocene compound is then contacted with the activator solution.

The mixture of the metallocene compound, activator and support is heated to about 0° C. to about 70° C., preferably to about 23° C. to about 60° C., preferably at room temperature. Contact times typically range from about 0.1 hour to about 24 hours, from about 2 hours to about 16 hours, or from about 4 hours to about 8 hours.

Suitable non-polar solvents are materials in which all of the reactants used herein, i.e., the activator, and the metallocene compound, are at least partially soluble and which are liquid at reaction temperatures. Preferred non-polar solvents are alkanes, such as isopentane, hexane, n-heptane, octane, nonane, and decane, although a variety of other materials including cycloalkanes, such as cyclohexane, aromatics, such as benzene, toluene, and ethylbenzene, may also be employed.

Polymerization Processes

In embodiments herein, the invention relates to polymerization processes where monomer (such as ethylene or propylene), and, optionally, comonomer, are contacted with a catalyst system comprising an activator and at least one metallocene compound, prepared as described herein. The catalyst compound and activator may be combined in any order, and are combined typically prior to contacting with the monomer.

Monomers useful herein include substituted or unsubstituted $C_2$ to $C_{40}$ α-olefins, preferably $C_2$ to $C_{20}$ α olefins, preferably $C_2$ to $C_{12}$ α olefins, preferably ethylene, propylene, butene, pentene, hexene, heptene, octene, nonene, decene, undecene, dodecene, and isomers thereof. In a preferred embodiment of the invention, the monomer comprises propylene and optional comonomers comprising one or more of ethylene or $C_4$ to $C_{40}$ olefins, preferably $C_4$ to $C_{20}$ olefins, or preferably $C_6$ to $C_{12}$ olefins. The $C_4$ to $C_{40}$ olefin monomers may be linear, branched, or cyclic. The $C_4$ to $C_{40}$ cyclic olefins may be strained or unstrained, monocyclic or polycyclic, and may optionally include heteroatoms and/or one or more functional groups. In another preferred embodiment, the monomer comprises ethylene and optional comonomer(s) comprising one or more $C_3$ to $C_{40}$ olefins, preferably $C_4$ to $C_{20}$ olefins, or preferably $C_6$ to $C_{12}$ olefins. The $C_3$ to $C_{40}$ olefin monomers may be linear, branched, or cyclic. The $C_3$ to $C_{40}$ cyclic olefins may be strained or unstrained, monocyclic or polycyclic, and may optionally include heteroatoms and/or one or more functional groups.

Exemplary $C_2$ to $C_{40}$ olefin monomers and optional comonomers include ethylene, propylene, butene, pentene, hexene, heptene, octene, nonene, decene, undecene, dodecene, norbornene, norbornadiene, di cyclopentadiene, cyclopentene, cycloheptene, cyclooctene, cyclooctadiene, cyclododecene, 7-oxanorbornene, 7-oxanorbornadiene, substituted derivatives thereof, and isomers thereof, preferably hexene, heptene, octene, nonene, decene, dodecene, cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, norbornadiene, and their respective homologs and derivatives, preferably norbornene, norbornadiene, and dicyclopentadiene.

Polymerization processes of this invention can be carried out in any manner known in the art. Any suspension, homogeneous, bulk, solution, slurry, or gas phase polymerization process known in the art can be used. Such processes can be run in a batch, semi-batch, or continuous mode. Homogeneous polymerization processes and slurry processes are preferred. (A homogeneous polymerization process is defined to be a process where at least 90 wt % of the product is soluble in the reaction media.) A bulk homogeneous process is particularly preferred. (A "bulk process" is defined to be a process where monomer concentration in all feeds to the reactor is 70 vol % or more.) Alternately, no solvent or diluent is present or added in the reaction medium (except for the small amounts used as the carrier for the catalyst system or other additives, or amounts typically found with the monomer; e.g., propane in propylene). In another embodiment, the process is a slurry process. As used herein the term "slurry polymerization process" means a polymerization process where a supported catalyst is employed and monomers are polymerized on the supported catalyst particles. At least 95 wt % of polymer products derived from the supported catalyst are in granular form as solid particles (not dissolved in the diluent).

Suitable diluents/solvents for polymerization include non-coordinating, inert liquids. Examples include straight and branched-chain hydrocarbons, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, such as can be found commercially (Isopar™); perhalogenated hydrocarbons, such as perfluorinated C4-10 alkanes, chlorobenzene, and aromatic and alkylsubstituted aromatic compounds, such as benzene, toluene, mesitylene, and xylene. Suitable solvents also include liquid olefins which may act as monomers or comonomers including ethylene, propylene, 1-butene, 1-hexene, 1-pentene, 3-methyl-1-pentene, 4-methyl-1-pentene, 1-octene, 1-decene, and mixtures thereof. In a preferred embodiment, aliphatic hydrocarbon solvents are used as the solvent, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In another embodiment, the solvent is not aromatic, preferably aromatics are present in the solvent at less than 1 wt %, preferably less than 0.5 wt %, preferably less than 0 wt %, based upon the weight of the solvents.

In a preferred embodiment, the feed concentration of the monomers and comonomers for the polymerization is 60 vol % solvent or less, preferably 40 vol % or less, or preferably 20 vol % or less, based on the total volume of the feedstream. Preferably, the polymerization is run in a bulk process.

Preferred polymerizations can be run at any temperature and/or pressure suitable to obtain the desired ethylene polymers. Typical temperatures and/or pressures include a temperature in the range of from about 0° C. to about 300° C., preferably from about 20° C. to about 200° C., preferably from about 35° C. to about 150° C., preferably from about 40° C. to about 120° C., preferably from about 45° C. to about 80° C.; and at a pressure in the range of from about 0.35 MPa to about 10 MPa, preferably from about 0.45 MPa to about 6 MPa, or preferably from about 0.5 MPa to about 4 MPa.

In a typical polymerization, the run time of the reaction is up to 300 minutes, preferably in the range of from about 5 to 250 minutes, or preferably from about 10 to 120 minutes.

Polyolefin Products

The process of this invention produces olefin polymers, preferably polyethylene and polypropylene homopolymers and copolymers. In one embodiment, the polymers produced herein are copolymers of ethylene preferably having from 0 to 25 mol % (alternately from 0.5 to 20 mol %, alternately from 1 to 15 mol %, preferably from 3 to 10 mol %) of one or more $C_3$ to $C_{20}$ olefin comonomer (preferably $C_3$ to $C_{12}$ α-olefin, preferably propylene, butene, hexene, octene, decene, dodecene, preferably propylene, butene, hexene, octene), or are copolymers of propylene preferably having from 0 to 25 mol % (alternately from 0.5 to 20 mol %, alternately from 1 to 15 mol %, preferably from 3 to 10 mol %) of one or more of $C_2$ or $C_4$ to $C_{20}$ olefin comonomer (preferably ethylene or $C_4$ to $C_{12}$ α-olefin, preferably ethylene, butene, hexene, octene, decene, dodecene, preferably ethylene, butene, hexene, octene).

In a preferred embodiment of the invention, the propylene polymers produced may be isotactic polypropylene, atactic polypropylene and random, block, or impact copolymers.

The polypropylene homopolymer or propylene copolymer produced herein may have some level of isotacticity, and is preferably isotactic or highly isotactic. As used herein, "isotactic" is defined as having at least 10% isotactic pentads according to analysis by $^{13}$C-NMR as described in US 2008/0045638 at paragraph [0613] et seq. As used herein, "highly isotactic" is defined as having at least 60% isotactic pentads according to analysis by $^{13}$C-NMR. In a desirable embodiment, a polypropylene homopolymer having at least 85% isotacticity, preferably at least 90% isotacticity is produced herein. In another embodiment, the propylene polymer produced may be atactic. Atactic polypropylene is defined to be less than 10% isotactic or syndiotactic pentads according to analysis by $^{13}$C-NMR.

Blends

In another embodiment, the polymer (preferably the polyethylene or polypropylene) produced herein is combined with one or more additional polymers prior to being formed into a film, molded part, or other article. Other useful polymers include polyethylene, isotactic polypropylene, highly isotactic polypropylene, syndiotactic polypropylene, random copolymer of propylene and ethylene, and/or butene, and/or hexene, polybutene, ethylene vinyl acetate, LDPE, LLDPE, HDPE, ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, cross linked polyethylene, copolymers of ethylene and vinyl alcohol (EVOH), polymers of aromatic monomers such as polystyrene, poly-1 esters, polyacetal, polyvinylidine fluoride, polyethylene glycols, and/or polyisobutylene.

In a preferred embodiment, the polymer (preferably the polyethylene or polypropylene) is present in the above blends, at from 10 to 99 wt %, based upon the weight of the polymers in the blend, preferably 20 to 95 wt %, even more preferably at least 30 to 90 wt %, even more preferably at least 40 to 90 wt %, even more preferably at least 50 to 90 wt %, even more preferably at least 60 to 90 wt %, even more preferably at least 70 to 90 wt %.

The blends described above may be produced by mixing the polymers produced as described herein with one or more polymers (as described above), by connecting reactors together in series to make reactor blends or by using more than one catalyst in the same reactor to produce multiple species of polymer. The polymers can be mixed together prior to being put into the extruder or may be mixed in an extruder.

The blends may be formed using conventional equipment and methods, such as by dry blending the individual components and subsequently melt mixing in a mixer, or by mixing the components together directly in a mixer, such as, for example, a Banbury mixer, a Haake mixer, a Brabender internal mixer, or a single or twin-screw extruder, which may include a compounding extruder and a side-arm extruder used directly downstream of a polymerization process, which may include blending powders or pellets of the resins at the hopper of the film extruder. Additionally, additives may be included in the blend, in one or more components of the blend, and/or in a product formed from the blend, such as a film, as desired. Such additives are well known in the art, and can include, for example: fillers; antioxidants (e.g., hindered phenolics such as IRGANOX™ 1010 or IRGANOX™ 1076 available from Ciba-Geigy); phosphites (e.g., IRGAFOS™ 168 available from Ciba-Geigy); anti-cling additives; tackifiers, such as polybutenes, terpene resins, aliphatic and aromatic hydrocarbon resins, alkali metal and glycerol stearates, and hydrogenated rosins; UV stabilizers; heat stabilizers; anti-blocking agents; release agents; anti-static agents; pigments; colorants; dyes; waxes; silica; fillers; talc; and the like.

Other embodiments of the invention can include:
1. A method for preparing partially hydrogenated annulated cyclopentadienyl complexes, comprising contacting:
(a) a complex of Formula (I):

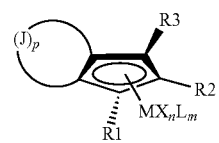

wherein:
J is C—R, CH, HC—R, $CR_2$ or $CH_2$, such that (J)p is $C_3$ to $C_{30}$ substituted or unsubstituted hydrocarbyl group having a chain of 3, 4, 5, or 6 carbons bound to the Cp to form an aromatic or pseudoaromatic 5, 6, 7, or 8 membered ring, which may be substituted or unsubstituted,
p is 3, 4, 5, or 6, preferably 3;
n is 1, 2, 3, 4, or 5;
m is 1, 2, 3, or 4;
M is a transition metal belonging to group 3, 4, 5, 6, or to the lanthanide or actinide groups of the Periodic Table of the Elements;
the X groups, the same or different from each other, are monoanionic ligands selected from the group consisting of hydrogen, halogen, —R, —OR, —OSO$_2$CF$_3$, —OCOR, —SR, —NR$_2$, and —PR$_2$ groups;
the R substituents, the same or different from each other, are linear or branched, saturated or unsaturated, $C_1$-$C_{20}$ alkyl, $C_3$-$C_{20}$ cycloalkyl, $C_6$-$C_{20}$ aryl, $C_7$-$C_{20}$ alkylaryl, or $C_7$-$C_{20}$ arylalkyl radicals, optionally containing one or more atoms belonging to Groups 13-17 of the Periodic Table of the Elements, and two R substituents may form a 5-7 membered ring;

the L groups, the same or different from each other, are neutral donor ligands; and $R^1$, $R^2$ and $R^3$ are each independently a hydrogen atom or a substituted or unsubstituted $C_1$ to $C_{20}$ hydrocarbyl group, and, optionally, $R^1$ and $R^2$ or $R^2$ and $R^3$ can be joined to form a cyclic structure; with (b) hydrogen and a hydrogenation catalyst to obtain a complex of Formula (II):

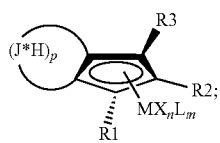

(II)

wherein:

M, X, L, n, m, p, R, $R^1$, $R^2$, $R^3$, are as defined for Formula (I) and J* is C, C—R, CH, such that $(J^*H)_p$ is a is $C_3$ to $C_{30}$ substituted or unsubstituted hydrocarbyl group having chain of 3, 4, 5, or 6 carbons bound to the Cp to form a substituted or unsubstituted saturated 5, 6, 7, or 8 membered ring.

2. The method of paragraph 1, wherein (J)p is —$(C_3H_4)$—, —$(C_4H_4)$—, —$(C_5H_6)$—, or —$(C_6H_6)$—).

3. The method of paragraph 1 or 2, wherein M is a group 4 metal.

4. The method of any of paragraphs 1 to 3, wherein M is Hf, Zr, or Ti.

5. The method of any of paragraphs 1 to 4, wherein X is a $C_1$ to $C_{20}$ alkyl or halogen, such as chlorine, bromine, iodine, fluorine, methyl, ethyl, propyl, butyl, pentyl, hexyl, heptyl, octyl, nonyl, decyl, undecyl, dodecyl, or an isomer thereof.

6. The method of any of paragraphs 1 to 5, wherein R is methyl, ethyl, propyl, butyl, pentyl, hexyl, heptyl, octyl, nonyl, decyl, undecyl, dodecyl, or an isomer thereof.

7. The method of any of paragraphs 1 to 6, wherein $R^1$, $R^2$, and $R^3$ are each independently methyl, ethyl, propyl, butyl, pentyl, hexyl, heptyl, octyl, nonyl, decyl, undecyl, dodecyl, or an isomer thereof.

8. The method of any of paragraphs 1 to 7, wherein (J*)p is —$(C_3H_6)$—, —$(C_4H_8)$—, —$(C_5H_{10})$—, —$(C_6H_{12})$—.

9. The method of any of paragraphs 1 to 8, wherein the complex of Formula (II) is prepared at a yield of at least 50%.

10. A method for preparing tetrahydroindenyl, comprising the steps of:

(a) contacting a complex of Formula (III):

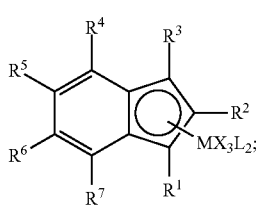

(III)

(b) with hydrogen and a hydrogenation catalyst to prepare a complex of Formula (IV):

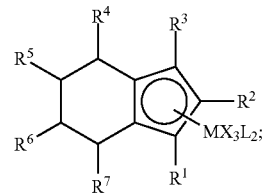

(IV)

wherein:

M is a transition metal belonging to group 3, 4, 5, 6, or to the lanthanide or actinide groups of the Periodic Table of the Elements;

the X groups, the same or different from each other, are monoanionic sigma ligands selected from the group consisting of hydrogen, halogen, —R, —OR, —$OSO_2CF_3$, —OCOR, —SR, —$NR_2$, and —$PR_2$ groups, wherein the R substituents are linear or branched, saturated or unsaturated, $C_1$-$C_{20}$ alkyl, $C_3$-$C_{20}$ cycloalkyl, $C_6$-$C_{20}$ aryl, $C_7$-$C_{20}$ alkylaryl, or $C_7$-$C_{20}$ arylalkyl radicals, optionally containing one or more atoms belonging to Groups 13-17 of the Periodic Table of the Elements, and two R substituents may form a 5-7 membered ring;

the L groups, the same or different from each other, are anionic leaving group ligands;

$R^1$, $R^2$, $R^3$, $R^4$, $R^5$, $R^6$, and $R^7$ are each independently a hydrogen atom or a substituted or unsubstituted $C_1$ to a $C_{20}$ hydrocarbyl group, and, optionally, any two of $R^5$, $R^6$, and $R^7$ can be joined to form a cyclic structure.

11. The method of paragraph 10, wherein the metal M is Zr, Hf, or Ti.

12. The method of paragraph 10 or 11, wherein X is a $C_1$ to $C_{20}$ alkyl or halogen, such as chlorine, bromine, iodine, fluorine, methyl, ethyl, propyl, butyl, pentyl, hexyl, heptyl, octyl, nonyl, decyl, undecyl, dodecyl, or an isomer thereof.

13. The method of any of paragraphs 10 to 12, wherein the X groups are Cl or Br.

14. The method of any of paragraphs 10 to 13, wherein $R^1$, $R^2$, $R^3$, $R^4$, $R^5$, $R^6$, and $R^7$ are each independently a $C_1$ to $C_{20}$ alkyl, such as methyl, ethyl, propyl, butyl, pentyl, hexyl, heptyl, octyl, nonyl, decyl, undecyl, dodecyl, or an isomer thereof.

15. The method of any of paragraphs 10 to 14, wherein $R^2$ is a substituted or unsubstituted $C_1$ to $C_{20}$ hydrocarbyl group (such as linear branched or cyclic methyl, ethyl, propyl, butyl, pentyl, hexyl, heptyl, octyl, nonyl, decyl, undecyl, or dodecyl, or an isomer thereof, preferably methyl).

16. The method of any of paragraphs 10 to 15, wherein $R^3$, $R^5$, $R^6$, and $R^7$ are each independently a hydrogen atom or a substituted or unsubstituted $C_1$ to $C_{20}$ hydrocarbyl group (such as linear branched or cyclic methyl, ethyl, propyl, butyl, pentyl, hexyl, heptyl, octyl, nonyl, decyl, undecyl, or dodecyl, or an isomer thereof), and, optionally, any two of $R^5$, $R^6$, and $R^7$ can be joined to form a cyclic structure.

17. The method of any of paragraphs 10 to 16, wherein $R^4$ is a substituted or unsubstituted aryl group (such as phenyl or phenyl substituted at 1, 2, or 3 positions with one or more of methyl, ethyl, propyl, butyl, pentyl, hexyl, heptyl, octyl, nonyl, decyl, undecyl, dodecyl, phenyl, substituted phenyl, or an isomer thereof).

18. The method of any of paragraphs 10 to 17, wherein the complex of Formula (IV) is prepared at a yield of at least 50%.

19. A method for preparing a metallocene catalyst, comprising the steps of: (a) contacting a complex of Formula (I):

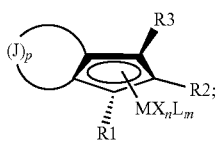

wherein: J, p, M, X, L, m, n, $R^1$, $R^2$, and $R^3$ are as described above; with hydrogen and a hydrogenation catalyst to obtain a complex of Formula (II):

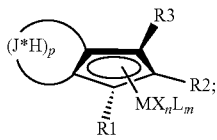

wherein: M, X, L, n, m, p, R, $R^1$, $R^2$, $R^3$, and J* are as described above; and (b) reacting the complex of Formula (II) with a substituted or unsubstituted cyclopentadiene to prepare a metallocene catalyst of Formula (III).

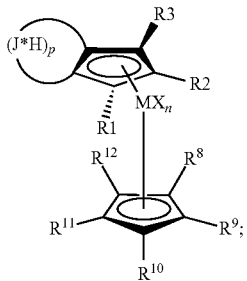

wherein: M, X, n, p, $R^1$, $R^2$, $R^3$, and J* are as described above and $R^8$, $R^9$, $R^{10}$, $R^{11}$, $R^{12}$, are independently as described for $R^1$.

20. A method for preparing a metallocene catalyst, comprising the steps of: (a) preparing a complex of Formula (III):

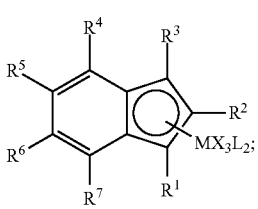

(b) reacting the complex of Formula (I) with hydrogen to prepare a complex of Formula (IV):

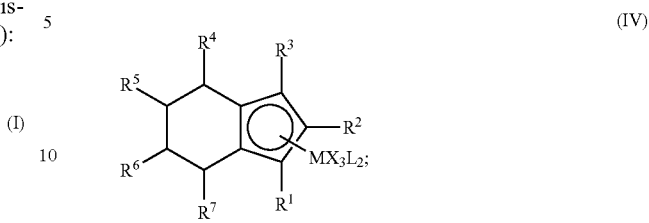

and
(c) reacting the complex of Formula (IV) with cyclopentadiene to prepare a metallocene catalyst of Formula (V):

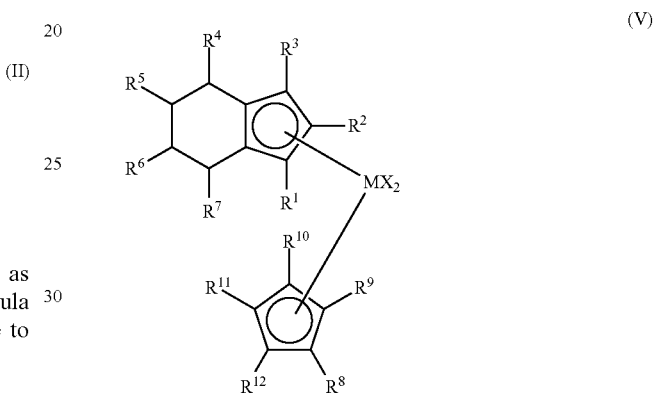

wherein: M is a transition metal belonging to group 3, 4, 5, 6, or to the lanthanide or actinide groups of the Periodic Table of the Elements (preferably Hf, Zr, or Ti);
the X groups, the same or different from each other, are monoanionic sigma ligands selected from the group consisting of hydrogen, halogen, —R, —OR, —OSO$_2$CF$_3$, —OCOR, —SR, —NR$_2$, and —PR$_2$ groups, wherein the R substituents are linear or branched, saturated or unsaturated, $C_1$-$C_{20}$ alkyl, $C_3$-$C_{20}$ cycloalkyl, $C_6$-$C_{20}$ aryl, $C_7$-$C_{20}$ alkylaryl, or $C_7$-$C_{20}$ arylalkyl radicals, optionally containing one or more atoms belonging to Groups 13-17 of the Periodic Table of the Elements, and two R substituents may form a 5-7 membered ring, preferably X is a $C_1$ to $C_{20}$ alkyl or halogen, such as chlorine, bromine, iodine, fluorine, methyl, ethyl, propyl, butyl, pentyl, hexyl, heptyl, octyl, nonyl, decyl, undecyl, dodecyl, or an isomer thereof; the L groups, the same or different from each other, are anionic leaving group ligands; $R^1$, $R^2$, $R^3$, $R^4$, $R^5$, $R^6$, $R^7$ $R^8$, $R^9$, $R^{10}$, $R^{11}$ and $R^{12}$, are each independently a hydrogen atom or a substituted or unsubstituted $C_1$ to a $C_{20}$ hydrocarbyl group, and, optionally, any two of $R^5$, $R^6$, and $R^7$ can be joined to form a cyclic structure, and any two of $R^8$, $R_9$, $R_{10}$, $R^{11}$, and $R^{12}$ adjacent to each other can be joined to form a cyclic structure, preferably X is a $C_1$ to $C_{20}$ alkyl, such as methyl, ethyl, propyl, butyl, pentyl, hexyl, heptyl, octyl, nonyl, decyl, undecyl, dodecyl or an isomer thereof, preferably, $R^2$ is a substituted or unsubstituted $C_1$ to a $C_{20}$ hydrocarbyl group (such as methyl, ethyl, propyl, butyl, pentyl, hexyl, heptyl, octyl, nonyl, decyl, undecyl, dodecyl, or an isomer thereof) and $R^4$ is a substituted or unsubstituted aryl group (such as phenyl or substituted phenyl); and $R_8$, $R_9$, $R_{10}$, $R_{11}$, and $R_{12}$ are each independently a substituted or unsubstituted $C_1$ to a $C_6$ hydrocarbyl group (such as methyl, ethyl, propyl, butyl, pentyl, or hexyl).

21. The method of paragraph 20, wherein the metal M is Zr or Hf.

22. The method of paragraph 20 or 21, wherein the X groups are Cl or Br.

23. The method of any of paragraphs 20 to 22, wherein $R^2$ is a primary substituted or unsubstituted $C_1$-$C_{12}$ alkyl group.

24. The method of any of paragraphs 20 to 23, wherein $R^4$ is selected from phenyl, 1-naphthyl, 2-naphthyl, 9-anthracenyl, 2-biphenyl, 3-biphenyl, 4-biphenyl, 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,5-trimethylphenyl, 3,4,5-trimethylphenyl, 2,3,4,5,6-pentamethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 3,5-diethylphenyl, 3-isopropylphenyl, 4-isopropylphenyl, 3,5-di-isopropylphenyl, 2,5-di-isopropylphenyl, 2-tert-butylphenyl, 3-tert-butylphenyl, 4-tert-butylphenyl, 3,5-di-tert-butylphenyl, 2,5-di-tert-butylphenyl, 2-trimethylsilylphenyl, 3-trimethylsilylphenyl, 4-trimethylsilylphenyl, 3,5-bis(trimethylsilyl)phenyl, 2-trifluoromethylphenyl, 3-trifluoromethylphenyl, 4-trifluoromethylphenyl, 3,5-bis(trifluoromethyl) phenyl, cyclopropyl, carbazolyl, indolyl, pyrrolyl, or 2-furanyl, 3-furanyl, 5-methyl-2-furanyl, 5-ethyl-2-furanyl, 4,5-dimethyl-2-furanyl, 2-methyl-3-furanyl, 5-methyl-3-furanyl, 2-thiophenyl, 3-thiophenyl, 5-methyl-2-thiophenyl, 2-methyl-3-thiophenyl, or 5-methyl-3-thiophenyl.

25. The method of any of paragraphs 20 to 24, wherein $R^3$ is a hydrogen atom.

26. The method of any of paragraphs 20 to 25, wherein $R^5$, $R^6$, and $R^7$ are independently a hydrogen atom or a substituted or unsubstituted $C_1$ to a $C_6$ hydrocarbyl group, and any two of $R^5$, $R^6$, and $R^7$ can be joined to form a cyclic structure.

27. The method of any of paragraphs 20 to 26, wherein $R^1$, $R^8$, $R^9$, $R^{10}$, $R^{11}$, and $R^{12}$, are independently a hydrogen atom or a substituted or unsubstituted $C_1$ to a $C_6$ hydrocarbyl group, and any two of $R^1$, $R^8$, $R^9$, $R^{10}$, $R^{11}$ and $R^{12}$ can be joined to form a cyclic structure.

28. A metallocene catalyst prepared according to the method of any of paragraphs 20 to 27.

29. A catalyst system comprising an activator and a metallocene catalyst of paragraph 28.

30. A process for preparing polyethylene comprising contacting ethylene with the catalyst system of paragraph 29 and obtaining polyethylene.

EXAMPLE

The invention, while not meant to be limited by, may be better understood by reference to the following example.

Preparation of (4,5,6,7-tetrahydroindenyl)zirconium trichloride dimethoxyethane

To a bright yellow solution of indenylzirconium trichloride dimethoxyethane (3.50 g, 8.69 mmol, 1.00 eq.) in dichloromethane (40 ml) was added platinum dioxide (0.175 g, 0.77 mmol, 5.0 wt %) to give a dirty yellow mixture. The mixture was stirred vigorously under 100 psi of hydrogen for 30 minutes. Hydrogen was vented and the mixture filtered to give a pale amber solution. The solution was evaporated under vacuum, leaving white solid. The solid was washed with pentane (2×30 ml) and dried under vacuum. Yield 3.18 g (90%). $^1$H NMR (CD$_2$Cl$_2$): δ 6.25 (t, 1H), 6.11 (d, 2H), 4.08 (br s, 4H), 3.86 (br s, 6H), 3.15 (m, 2H), 2.64 (m, 2H), 1.84 (m, 2H), 1.64 (m, 2H).

The remarkable advantage of the inventive method in preparation of tetrahydroindenyl zirconium complexes of (H$_4$Ind)ZrCl$_3$(dme) as demonstrated by a yield of as high as 90% over that of the conventional synthesis route starting from lithium tetrahydroindenide of only about 6% can render a promising alternative route to facilitate efficient synthesis of metallocene catalysts for olefin polymerization.

All documents described herein are fully incorporated herein by reference, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise, whenever a composition, an element or a group of elements is preceded with the transitional phrase "comprising," it is understood that we also contemplate the same composition or group of elements with transitional phrases "consisting essentially of" "consisting of," "selected from the group consisting of" or "is" preceding the recitation of the composition, element, or elements, and vice versa.

What is claimed is:
1. A method for preparing partially hydrogenated annulated cyclopentadienyl complexes, comprising contacting:
(a) a complex of Formula (I):

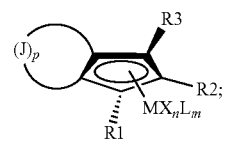

(I)

wherein
J is C—R, CH, HC—R, CR$_2$ or CH$_2$, such that (J)p is $C_3$ to $C_{30}$ substituted or unsubstituted hydrocarbyl group having a chain of 3, 4, 5, or 6 carbons bound to the Cp to form an aromatic or pseudoaromatic 5, 6, 7, or 8 membered ring, which may be substituted or unsubstituted,
p is 3, 4, 5, or 6;
n is 1, 2, 3, 4, or 5;
m is 1, 2, 3, or 4;
M is a transition metal belonging to group 3, 4, 5, 6, or to the lanthanide or actinide groups of the Periodic Table of the Elements;
the X groups, the same or different from each other, are monoanionic ligands selected from the group consisting of hydrogen, halogen, —R, —OR, —OSO$_2$CF$_3$, —OCOR, —SR, —NR$_2$, and —PR$_2$ groups;
the R substituents, the same or different from each other, are linear or branched, saturated or unsaturated, $C_1$-$C_{20}$ alkyl, $C_3$-$C_{20}$ cycloalkyl, $C_6$-$C_{20}$ aryl, $C_7$-$C_{20}$ alkylaryl, or $C_7$-$C_{20}$ arylalkyl radicals, optionally containing one or more atoms belonging to Groups 13-17 of the Periodic Table of the Elements, and two R substituents may form a 5-7 membered ring;

the L groups, the same or different from each other, are neutral donor ligands; and $R^1$, $R^2$ and $R^3$ are each independently a hydrogen atom or a substituted or unsubstituted $C_1$ to a $C_{20}$ hydrocarbyl group, and, optionally, $R^1$ and $R^2$ or $R^2$ and $R^3$ can be joined to form a cyclic structure; with (b) hydrogen and a hydrogenation catalyst to obtain a complex of Formula (II):

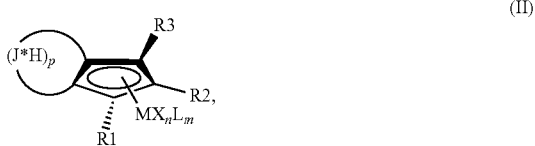

(II)

wherein:

M, X, L, n, m, p, R, $R^1$, $R^2$, $R^3$, are as defined for Formula (I) and J* is C, C—R, CH, such that $(J*H)_p$ is a $C_3$ to $C_{30}$ substituted or unsubstituted hydrocarbyl group having a chain of 3, 4, 5, or 6 carbons bound to the Cp to form a substituted or unsubstituted saturated 5, 6, 7, or 8 membered ring.

2. The method of claim 1, wherein (J)p is —($C_3H_4$)—, —($C_4H_4$)—, —($C_5H_6$)—, or —($C_6H_6$)—), and/or M is a group 4 metal, and/or M is Hf, Zr, or Ti, and/or X is a $C_1$ to $C_{20}$ alkyl or halogen, and/or R is methyl, ethyl, propyl, butyl, pentyl, hexyl, heptyl, octyl, nonyl, decyl, undecyl, dodecyl, or an isomer thereof, and/or $R^1$, $R^2$, and $R^3$ are each independently methyl, ethyl, propyl, butyl, pentyl, hexyl, heptyl, octyl, nonyl, decyl, undecyl, dodecyl, or an isomer thereof.

3. The method of claim 1, wherein (J*)p is —($C_3H_6$)—, —($C_4H_8$)—, —($C_5H_{10}$)—, or —($C_6H_{12}$).

4. The method of claim 1, wherein the complex of Formula (II) is prepared at a yield of at least 50%.

5. A method for preparing tetrahydroindenyl, comprising the steps of:

(a) contacting a complex of Formula (III):

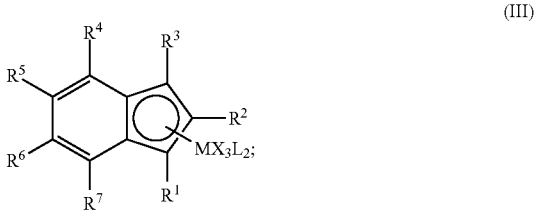

(III)

(b) with hydrogen and a hydrogenation catalyst to prepare a complex of Formula (IV):

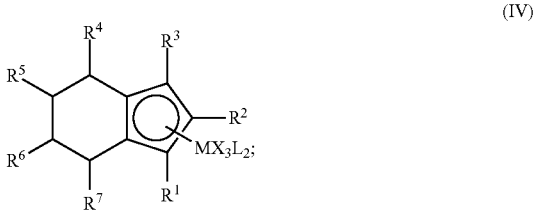

(IV)

wherein:

M is a transition metal belonging to group 3, 4, 5, 6, or to the lanthanide or actinide groups of the Periodic Table of the Elements;

the X groups, the same or different from each other, are monoanionic sigma ligands selected from the group consisting of hydrogen, halogen, —R, —OR, —$OSO_2CF_3$, —OCOR, —SR, —$NR_2$, and —$PR_2$ groups, wherein the R substituents are linear or branched, saturated or unsaturated, $C_1$-$C_{20}$ alkyl, $C_3$-$C_{20}$ cycloalkyl, $C_6$-$C_{20}$ aryl, $C_7$-$C_{20}$ alkylaryl, or $C_7$-$C_{20}$ arylalkyl radicals, optionally containing one or more atoms belonging to Groups 13-17 of the Periodic Table of the Elements, and two R substituents may form a 5-7 membered ring;

the L groups, the same or different from each other, are anionic leaving group ligands;

$R^1$, $R^2$, $R^3$, $R^4$, $R^5$, $R^6$, and $R^7$ are each independently a hydrogen atom or a substituted or unsubstituted $C_1$ to a $C_{20}$ hydrocarbyl group, and, optionally, any two of $R^5$, $R^6$, and $R^7$ can be joined to form a cyclic structure.

6. The method of claim 5, wherein the metal M is Zr, Hf, or Ti, and/or X is a $C_1$ to $C_{20}$ alkyl or halogen.

7. The method of claim 5, wherein the X groups are Cl or Br.

8. The method of claim 5, wherein $R^1$, $R^2$, $R^3$, $R^4$, $R^5$, $R^6$, and $R^7$ are each independently a $C_1$ to $C_{20}$ alkyl.

9. The method of claim 5, wherein $R^2$ is a substituted or unsubstituted $C_1$ to a $C_{20}$ hydrocarbyl group.

10. The method of claim 5, wherein $R^3$, $R^5$, $R^6$, and $R^7$ are each independently a hydrogen atom or a substituted or unsubstituted $C_1$ to a $C_{20}$ hydrocarbyl group, and, optionally, any two of $R^5$, $R^6$, and $R^7$ can be joined to form a cyclic structure.

11. The method of claim 5, wherein $R^4$ is a substituted or unsubstituted aryl group.

12. The method of claim 5, wherein the complex of Formula (IV) is prepared at a yield of at least 50%.

13. A method for preparing a metallocene catalyst, comprising reacting a complex represented by the Formula (II) of claim 1 with a substituted or unsubstituted cyclopentadiene to prepare a metallocene catalyst of Formula (VI):

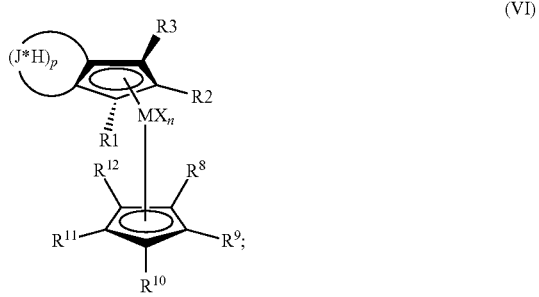

(VI)

wherein: M, X, n, p, $R^1$, $R^2$, $R^3$, and J* are as described in claim 1 and $R^8$, $R^9$, $R^{10}$, $R^{11}$, $R^{12}$, are independently as described for $R^1$.

14. A method for preparing a metallocene catalyst, comprising reacting a complex represented by Formula (IV) of claim 5 with cyclopentadiene to prepare a metallocene catalyst of Formula (V):

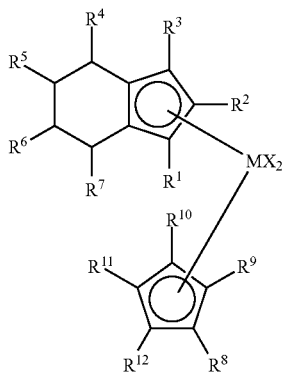

(V)

wherein: M is a transition metal belonging to group 3, 4, 5, 6, or to the lanthanide or actinide groups of the Periodic Table of the Elements (preferably Hf, Zr, or Ti);

the X groups, the same or different from each other, are monoanionic sigma ligands selected from the group consisting of hydrogen, halogen, —R, —OR, —OSO$_2$CF$_3$, —OCOR, —SR, —NR$_2$, and —PR$_2$ groups, wherein the R substituents are linear or branched, saturated or unsaturated, C$_1$-C$_{20}$ alkyl, C$_3$-C$_{20}$ cycloalkyl, C$_3$-C$_{20}$ aryl, C$_7$-C$_{20}$ alkylaryl, or C$_7$-C$_{20}$ arylalkyl radicals, optionally containing one or more atoms belonging to Groups 13-17 of the Periodic Table of the Elements, and two R substituents may form a 5-7 membered ring; and $R^1$, $R^2$, $R^3$, $R^4$, $R^5$, $R^6$, $R^7$ $R^8$, $R^9$, $R^{10}$, $R^{11}$ and $R^{12}$, are each independently a hydrogen atom or a substituted or unsubstituted C$_1$ to a C$^{20}$ hydrocarbyl group, and, optionally, any two of $R^5$, $R^6$, and $R^7$ can be joined to form a cyclic structure and any two of $R^8$, $R^9$, $R^{10}$, $R^{11}$, and $R^{12}$ adjacent to each other can be joined to form a cyclic structure.

15. The method of claim 14, wherein the metal M is Zr or Hf.

16. The method of claim 14, wherein the X groups are Cl or Br.

17. The method of claim 14, wherein $R^2$ is a primary substituted or unsubstituted C$_1$-C$_{12}$ alkyl group.

18. The method of claim 14, wherein $R^4$ is selected from phenyl, 1-naphthyl, 2-naphthyl, 9-anthracenyl, 2-biphenyl, 3-biphenyl, 4-biphenyl, 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,5-trimethylphenyl, 3,4,5-trimethylphenyl, 2,3,4,5,6-pentamethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 3,5-diethylphenyl, 3-isopropylphenyl, 4-isopropylphenyl, 3,5-di-isopropylphenyl, 2,5-di-isopropylphenyl, 2-tert-butylphenyl, 3-tert-butylphenyl, 4-tert-butylphenyl, 3,5-di-tert-butylphenyl, 2,5-di-tert-butylphenyl, 2-trimethylsilylphenyl, 3-trimethylsilylphenyl, 4-trimethylsilylphenyl, 3,5-bis(trimethylsilyl)phenyl, 2-trifluoromethylphenyl, 3-trifluoromethylphenyl, 4-trifluoromethylphenyl, 3,5-bis(trifluoromethyl)phenyl, cyclopropyl, carbazolyl, indolyl, pyrrolyl, or 2-furanyl, 3-furanyl, 5-methyl-2-furanyl, 5-ethyl-2-furanyl, 4,5-dimethyl-2-furanyl, 2-methyl-3-furanyl, 5-methyl-3-furanyl, 2-thiophenyl, 3-thiophenyl, 5-methyl-2-thiophenyl, 2-methyl-3-thiophenyl, or 5-methyl-3-thiophenyl.

19. The method of claim 14, wherein $R^3$ is a hydrogen atom.

20. The method of claim 14, wherein $R^5$, $R^6$, and $R^7$ are independently a hydrogen atom or a substituted or unsubstituted C$_1$ to a C$_6$ hydrocarbyl group, and any two of $R^5$, $R^6$, and $R^7$ can be joined to form a cyclic structure.

21. The method of claim 14, wherein $R^1$, $R^8$, $R^9$, $R^{10}$, $R^{11}$, and $R^{12}$, are independently a hydrogen atom or a substituted or unsubstituted C$_1$ to a C$_6$ hydrocarbyl group, and any two of $R^1$, $R^8$, $R^9$, $R^{10}$, $R^{11}$, and $R^{12}$ can be joined to form a cyclic structure.

22. A metallocene catalyst prepared according to the method of claim 14.

23. A catalyst system comprising an activator and a metallocene catalyst of claim 22.

24. A process for preparing polyethylene comprising contacting ethylene with the catalyst system of claim 23.

25. The method of claim 14 wherein X is methyl, ethyl, propyl, butyl, pentyl, hexyl, heptyl, octyl, nonyl, decyl, undecyl, dodecyl, or an isomer thereof, $R^2$ is methyl, ethyl, propyl, butyl, pentyl, hexyl, heptyl, octyl, nonyl, decyl, undecyl, dodecyl, or an isomer thereof and $R^4$ is phenyl or substituted phenyl.

* * * * *